US 6,610,629 B2

(12) United States Patent
Hinago et al.

(10) Patent No.: US 6,610,629 B2
(45) Date of Patent: Aug. 26, 2003

(54) PROCESS FOR PRODUCING AN OXIDE CATALYST FOR OXIDATION OR AMMOXIDATION

(75) Inventors: Hidenori Hinago, Kurashiki (JP); Hiroyuki Yano, Kurashiki (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 09/953,970

(22) Filed: Sep. 18, 2001

(65) Prior Publication Data

US 2003/0017944 A1 Jan. 23, 2003

(30) Foreign Application Priority Data

Sep. 18, 2000 (JP) ........................................ 2000-281947

(51) Int. Cl.⁷ .......................... B01J 23/00; B01J 21/02; C07F 9/00; C07C 253/00; C07C 51/16
(52) U.S. Cl. ...................... 502/300; 502/202; 502/205; 502/206; 502/211; 502/212; 502/215; 502/305; 502/311; 502/312; 556/42; 556/47; 558/318; 558/319; 562/547
(58) Field of Search .......................... 502/300, 202–215, 502/232–263, 302–349, 351–355; 556/42, 47; 558/318, 319; 562/547

(56) References Cited

U.S. PATENT DOCUMENTS

| | | | | |
|---|---|---|---|---|
| 4,174,459 A | * | 11/1979 | Sakamoto et al. ........... | 562/534 |
| 4,568,790 A | * | 2/1986 | McCain ....................... | 585/658 |
| 5,231,214 A | * | 7/1993 | Ushikubo et al. ........... | 558/319 |
| 5,422,328 A | * | 6/1995 | Ushikubo et al. ........... | 502/312 |
| 5,750,777 A | * | 5/1998 | Aubry et al. ................ | 562/549 |
| 6,036,880 A | * | 3/2000 | Komada et al. ......... | 252/183.13 |
| 6,143,690 A | * | 11/2000 | Komada et al. ............. | 502/211 |
| 6,143,916 A | * | 11/2000 | Hinago et al. .............. | 558/321 |
| 6,291,393 B1 | * | 9/2001 | Tu et al. ...................... | 502/311 |
| 6,346,647 B2 | * | 2/2002 | Tu et al. ...................... | 562/549 |
| 6,383,978 B1 | * | 5/2002 | Bogan, Jr. .................. | 502/311 |
| 6,407,280 B1 | * | 6/2002 | Chaturvedi et al. ......... | 558/319 |
| 6,432,870 B1 | * | 8/2002 | Tu et al. ...................... | 502/305 |

FOREIGN PATENT DOCUMENTS

| | | | |
|---|---|---|---|
| JP | 11-226408 | 8/1999 | |
| JP | 11-285636 | * 10/1999 | ............ B01J/23/28 |
| WO | WO 00/12209 | 9/2000 | |

* cited by examiner

Primary Examiner—Mark L. Bell
Assistant Examiner—Patricia L. Hailey
(74) Attorney, Agent, or Firm—Birch, Stewart, Kolasch & Birch, LLP

(57) ABSTRACT

Disclosed is a process for producing an oxide catalyst comprising, as component elements, molybdenum (Mo), vanadium (V), at least one element selected from the group consisting of the two elements of antimony (Sb) and tellurium (Te), and niobium (Nb), wherein the process comprises providing an aqueous raw material mixture containing compounds of the component elements of the oxide catalyst, and drying the aqueous raw material mixture, followed by calcination, and wherein, in the aqueous raw material mixture, at least a part of the niobium compound as one of the compounds of the component elements is present in the form of a complex thereof with a complexing agent comprising a compound having a hydroxyl group bonded to an oxygen atom or a carbon atom. Also disclosed is a process for producing (meth)acrylonitrile or (meth)acrylic acid, which comprises performing the ammoxidation or oxidation of propane or isobutane in the gaseous phase in the presence of the oxide catalyst.

13 Claims, No Drawings

PROCESS FOR PRODUCING AN OXIDE CATALYST FOR OXIDATION OR AMMOXIDATION

BACKGROUND OF THE INVENTION

1. Field of the Invention

The present invention relates to a process for producing an oxide catalyst for use in a catalytic oxidation or ammoxidation of propane or isobutane in the gaseous phase. More particularly, the present invention is concerned with a process for producing an oxide catalyst comprising, as component elements, molybdenum (Mo), vanadium (V), at least one element selected from the group consisting of the two elements of antimony (Sb) and tellurium (Te), and niobium (Nb), wherein the process comprises providing an aqueous raw material mixture containing compounds of the component elements of the oxide catalyst, and drying the aqueous raw material mixture, followed by calcination, and wherein, in the aqueous raw material mixture, at least a part of the niobium compound as one of the compounds of the component elements is present in the form of a complex thereof with a complexing agent comprising a compound having a hydroxyl group bonded to an oxygen atom or a carbon atom. When the ammoxidation or oxidation of propane or isobutane in the gaseous phase is performed in the presence of the oxide catalyst produced by the process of the present invention, (meth)acrylonitrile or (meth)acrylic acid can be produced at a relatively low reaction temperature with high selectivity and in high yield as well as in high space time yield. Further, by the use of the process of the present invention for producing an oxide catalyst, precipitation of the niobium compound during the step for producing the aqueous raw material mixture can be reduced or substantially prevented, so that the aqueous raw material mixture can be obtained in the form of a low viscosity slurry having a low solids content or in the form of an aqueous solution. Therefore, the process of the present invention for producing an oxide catalyst is advantageous not only in that the motive power needed for agitation in tanks for producing or storing the aqueous raw material mixture can be reduced, but also in that precipitation of the niobium compound in the tanks or transfer pipes (which causes disadvantageous phenomena, such as formation of an aqueous raw material mixture having a non-uniform compositional distribution and occurrence of a clogging in the tanks or transfer pipes) can be reduced or substantially prevented without using any special equipment. Therefore, by the process of the present invention, the production of an oxide catalyst can be performed efficiently, as compared to the case of the use of conventional processes for producing an oxide catalyst. The present invention is also concerned with a process for producing (meth)acrylonitrile or (meth)acrylic acid, which comprises performing the ammoxidation or oxidation of propane or isobutane in the gaseous phase in the presence of the oxide catalyst.

2. Prior Art

Conventionally, there have been well known a process for producing (meth)acrylonitrile by ammoxidation of propylene or isobutylene, and a process for producing (meth)acrylic acid by oxidation of propylene or isobutylene. Recently, as substitutes for such processes for the oxidation and ammoxidation of propylene or isobutylene, attention has been attracted to a process for producing (meth)acrylonitrile by a catalytic ammoxidation of propane or isobutane in the gaseous phase, and a process for producing (meth)acrylic acid by a catalytic oxidation of propane or isobutane. As catalysts for use in these processes, a number of oxide catalysts have been proposed.

Of the oxide catalysts proposed, especially, an oxide catalyst comprising Mo—V—Te—Nb or Mo—V—Sb—Nb has been attracting attention, since such an oxide catalyst can be used for producing (meth)acrylonitrile or (meth)acrylic acid at a low reaction temperature with relatively high selectivity and in relatively high yield. Such an oxide catalyst is disclosed in various patent documents, such as Unexamined Japanese Patent Application Laid-Open Specification Nos. 2-257 (corresponding to U.S. Pat. No. 5,049,692 and EP 0318295 B1), 5-148212 (corresponding to U.S. Pat. No. 5,231,214 and EP 0512846 B1), 5-208136 (corresponding to U.S. Pat. No. 5,281,745 and EP 0529853 B1), 6-227819, 6-285372 (corresponding to U.S. Pat. No. 5,422,328 and EP 0603836 B1), 7-144132, 7-232071, 8-57319, 8-141401, 9-157241 (corresponding to U.S. Pat. No. 5,750,760 and EP 0767164 B1), 10-310539, 10-330343, 11-42434, 11-169716, 11-226408, 2000-143244, 11-47598 (corresponding to U.S. Pat. No. 6,036,880), 11-239725 (corresponding to U.S. Pat. No. 6,603,728), 2000-70714 (corresponding to WO 0012209 A1), U.S. Pat. No. 6,043,185, 9-316023, 10-118491, 10-120617 (corresponding to FR 2754817 A1), 9-278680 and 10-128112.

With respect to niobium sources for use in the production of the oxide catalyst comprising Mo—V—Te—Nb or Mo—V—Sb—Nb, the above-mentioned patent documents describe an aqueous solution of ammonium niobium oxalate; an aqueous solution obtained by dissolving a niobic acid in an aqueous oxalic acid solution; an aqueous solution of niobium oxalate; an aqueous solution of niobium hydrogenoxalate; $Nb_2O_5$; $NbCl_5$; $NbCl_3$; $Nb(OC_2H_5)_5$; $Nb_2(C_2O_4)_5$; and a niobic acid.

With respect to niobium sources used in the above-mentioned patent documents for preparing an aqueous raw material mixture used in the production of the oxide catalyst, among the above-mentioned niobium sources, the niobium-containing aqueous solutions (i.e., the aqueous ammonium niobium oxalate solution, the aqueous solution obtained by dissolving niobic acid in an aqueous oxalic acid solution and an aqueous niobium oxalate solution, each of which is a niobium source containing a water-soluble niobium compound) are used. In the above-mentioned patent documents, each of these niobium-containing aqueous solutions is mixed with an aqueous solution containing compounds of component elements Mo, V and Sb or with an aqueous solution containing compounds of component elements Mo, V and Te, thereby producing the aqueous raw material mixture for use in the production of the oxide catalyst.

However, these niobium-containing aqueous solutions have a problem in that, when an aqueous raw material mixture is produced by mixing any of the above-mentioned niobium-containing aqueous solutions with an aqueous solution containing compounds of Mo, V and Sb or with an aqueous solution containing compounds of Mo, V and Te, almost all of the niobium atoms precipitate in the form of niobium compounds, such as niobium hydroxide, so that an oxide catalyst produced from the obtained aqueous raw material mixture cannot exhibit satisfactory performance when used in a catalytic ammoxidation or oxidation of propane or isobutane in the gaseous phase for producing (meth)acrylonitrile or (meth)acrylic acid. Further, due to the precipitation of the niobium compounds, the aqueous raw material mixture is obtained in the form of a slurry. Therefore, disadvantages are likely to occur that a large motive power is needed for agitation in tanks for producing or storing the aqueous raw material mixture, and that the compositional distribution of the aqueous raw material mixture becomes non-uniform or a clogging occurs in the tanks or transfer pipes due to the precipitation of the niobium compounds therein and, hence, the use of special equipment (such as specially designed pipes) is needed to prevent such precipitation of the niobium compounds. Such disadvantages are serious problems in a commercial scale production of an oxide catalyst.

Unexamined Japanese Patent Application Laid-Open Specification No. 7-315842 discloses a process comprising mixing an aqueous solution of ammonium niobium oxalate with an aqueous solution containing compounds of Mo, V and Te to produce an aqueous raw material mixture and, before precipitation of the niobium compounds begins, spray-drying the aqueous raw material mixture. However, this patent document describes that precipitation of the niobium compounds begins about 10 minutes after completion of the production of the aqueous raw material mixture. Therefore, it is difficult to employ the process of this patent document in a commercial scale production of an oxide catalyst.

In an attempt to obtain an aqueous raw material mixture capable of maintaining the state of an aqueous solution, Unexamined Japanese Patent Application Laid-Open Specification No. 2000-24501 (corresponding to EP 0962253 A2) proposes a process in which each of an aqueous solution of niobium oxalate and an aqueous solution containing compounds of Mo, V and Te is individually diluted with a large amount of water, whereupon the diluted aqueous solution of niobium oxalate is mixed with the diluted aqueous solution containing compounds of Mo, V and Te, thereby producing a aqueous raw material mixture in the form of a low concentration aqueous solution. However, in the process of this patent document, the transformation of the aqueous raw material mixture (obtained in the form of an aqueous solution) into a slurry begins only about 5 minutes after completion of the production of the aqueous raw material mixture, and almost all of the niobium atoms in the aqueous raw material mixture precipitate in the form of niobium compounds (such as niobium hydroxide) only about 15 minutes after completion of the production of the aqueous raw material mixture. That is, by the process of this patent document, the transformation of the aqueous raw material mixture (obtained in the form of an aqueous solution) into a slurry is delayed only slightly, and it is impossible to obtain an aqueous raw material mixture which can stably maintain the state of an aqueous solution. Therefore, it is difficult to employ the process of this patent document in a commercial scale production of an oxide catalyst. Further, the process is disadvantageous in that the use of a large amount of water for the dilution of the aqueous solutions necessitates the use of a large amount of energy for drying the aqueous raw material mixture. Furthermore, when it is attempted to apply the technique of this patent document to a catalytic ammoxidation or oxidation of propane or isobutane performed in a fluidized bed reactor, the following problem arises. In the case of a catalytic ammoxidation or oxidation of propane or isobutane performed in a fluidized bed reactor, for the purpose of improving the fluidity of a catalyst, the catalyst is required to be in the form of spherical particles. For obtaining a catalyst precursor which can be used to obtain a catalyst in the form of spherical particles, the aqueous raw material mixture is spray dried. However, when the aqueous raw material mixture obtained by the process of the above patent document, which contains a large amount of water, is spray dried to obtain a catalyst precursor, the resultant catalyst particles are likely to have disadvantageously irregular non-spherical shapes.

Each of Unexamined Japanese Patent Application Laid-Open Specification Nos. 11-285636 and 2000-70714 (corresponding to WO 0012209 A1) discloses a process for producing an oxide catalyst by the use of an aqueous raw material mixture which is obtained by subjecting an aqueous solution containing compounds of Mo, V and Sb to an oxidation treatment, followed by addition of an aqueous solution of niobium oxalate, wherein the oxidation treatment is performed by adding aqueous hydrogen peroxide to the aqueous solution containing compounds of Mo, V and Sb. Specifically, the oxidation treatment is performed by a method in which Sb having a valence of 3, V having a valence of 5 and Mo having a valence of 6 are subjected to a redox in an aqueous solution, followed by addition of aqueous hydrogen peroxide, to thereby perform an oxidation treatment of reduced elements. With respect to the oxidation treatment, the above-mentioned Unexamined Japanese Patent Application Laid-Open Specification No. 11-285636 describes a method in which aqueous hydrogen peroxide is dropwise added to a 100° C. aqueous solution containing compounds of elements Mo, V and Sb, such that the resultant aqueous solution has a hydrogen peroxide/Sb molar ratio of about 0.5 or less. On the other hand, the above-mentioned Unexamined Japanese Patent Application Laid-Open Specification No. 2000-70714 describes a method in which aqueous hydrogen peroxide is dropwise added to a 25° C. aqueous solution containing compounds of Mo, V and Sb, such that the resultant aqueous solution has a hydrogen peroxide/Sb molar ratio of about 0.8. The processes of Unexamined Japanese Patent Application Laid-Open Specification Nos. 11-285636 and 2000-70714 have a problem in that, when the aqueous solution of niobium oxalate is added, after the oxidation treatment, to the aqueous solution containing compounds of Mo, V and Sb, almost all of the niobium atoms precipitate in the form of niobium compounds (such as niobium hydroxide), which is disadvantageous for a large-scale production of an oxide catalyst. Further, the oxide catalyst produced by any of these processes is disadvantageous in that the results (selectivity, yield and the like) of a catalytic oxidation or ammoxidation performed in the presence of the oxide catalyst is unsatisfactory.

In the above-mentioned Unexamined Japanese Patent Application Laid-Open Specification No. 11-226408, an aqueous solution containing compounds of Mo, V and Te or an aqueous solution containing compounds of Mo, V and Sb is prepared as follows. To an aqueous solution of ammonium paramolybdate is added a tellurium powder or an antimony powder, followed by addition of aqueous hydrogen peroxide. The resultant aqueous mixture is stirred at 70° C. to dissolve the tellurium powder or the antimony powder, thereby obtaining a homogeneous solution. To the obtained homogeneous solution is added ammonium metavanadate to dissolve the ammonium metavanadate in the homogeneous solution, thereby preparing an aqueous solution containing compounds of Mo, V and Te or an aqueous solution containing compounds of Mo, V and Sb. Subsequently, an aqueous solution of ammonium niobium oxalate is added to the prepared aqueous solution, to thereby obtain an aqueous raw material mixture. An oxide catalyst is produced using the obtained raw material mixture. Also in this method, almost all of the niobium atoms contained in the aqueous ammonium niobium oxalate solution precipitate in the form of niobium compounds (such as niobium hydroxide), which is disadvantageous for a large-scale production of an oxide catalyst. Further, there is also a problem in that the results (selectivity, yield and the like) of a catalytic oxidation or ammoxidation performed in the presence of the oxide catalyst is unsatisfactory.

Thus, each of the conventional processes for producing an oxide catalyst comprising, as component elements, molybdenum (Mo), vanadium (V), at least one element selected from the group consisting of the two elements of antimony (Sb) and tellurium (Te), and niobium (Nb) has problems in that the process is not suitable for a large-scale production of an oxide catalyst, and that satisfactorily high selectivity or yield cannot be achieved when a catalytic oxidation or ammoxidation is conducted in the presence of the obtained oxide catalyst.

SUMMARY OF THE INVENTION

In this situation, the present inventors have made extensive and intensive studies toward solving the above-mentioned problems accompanying the prior art. As a result, it has unexpectedly been found that the objective can be attained by a process for producing an oxide catalyst comprising, as component elements, molybdenum (Mo), vanadium (V), at least one element selected from the group consisting of the two elements of antimony (Sb) and tellurium (Te), and niobium (Nb), wherein the process uses an aqueous raw material mixture in which at least a part of the niobium compound as one of the compounds of the component elements is present in the form of a complex thereof with a complexing agent comprising a compound having a hydroxyl group bonded to an oxygen atom or a carbon atom. Specifically, the present inventors have found that, by the use of the above-mentioned process for producing an oxide catalyst, the precipitation of the niobium compound during the step for producing the aqueous raw material mixture can be reduced or substantially prevented. In addition, it has surprisingly been found that, when the oxide catalyst produced by the above-mentioned process is used for producing (meth)acrylonitrile or (meth)acrylic acid, a great improvement can be obtained in the selectivity for and the yield of the desired product as well as in the space time yield of the desired product.

The present invention has been completed, based on these novel findings.

Accordingly, it is a primary object of the present invention to provide a process for producing an oxide catalyst for use in a catalytic ammoxidation of propane or isobutane in the gaseous phase for producing (meth)acrylonitrile, or a catalytic oxidation of propane or isobutane in the gaseous phase for producing (meth)acrylic acid, wherein the oxide catalyst comprises, as component elements, molybdenum, vanadium, at least one element selected from the group consisting of the two elements of antimony and tellurium, and niobium, and wherein the process is advantageous not only in that, when the oxide catalyst produced by the process is used for producing (meth)acrylonitrile or (meth)acrylic acid, a great improvement can be obtained in the selectivity for and the yield of the desired product as well as in the space time yield of the desired product, but also in that the process is suitable for large scale, commercial production of the oxide catalyst.

Another object of the present invention is to provide a process for producing (meth)acrylonitrile, comprising performing ammoxidation of propane or isobutane in the presence of the above-mentioned oxide catalyst, and a process for producing (meth)acrylic acid, comprising performing oxidation of propane or isobutane in the presence of the above-mentioned oxide catalyst.

The foregoing and other objects, and advantages of the present invention will be apparent to those skilled in the art from the following detailed description taken in connection with the appended claims.

DETAILED DESCRIPTION OF THE INVENTION

In one aspect of the present invention, there is provided a process for producing an oxide catalyst for use in a catalytic oxidation or ammoxidation of propane or isobutane in the gaseous phase, wherein the oxide catalyst comprises a composition represented by the following formula (I)

$$MO_{1.0}V_aX_bNb_cZ_dO_n \qquad (I)$$

wherein:
X is at least one element selected from the group consisting of antimony and tellurium;
Z is at least one element selected from the group consisting of tungsten, chromium, titanium, aluminum, tantalum, zirconium, hafnium, manganese, rhenium, iron, ruthenium, cobalt, rhodium, nickel, palladium, platinum, zinc, boron, gallium, indium, germanium, tin, phosphorus, lead, bismuth, yttrium, rare earth elements and alkaline earth metals; and
a, b, c, d, and n are, respectively, the atomic ratios of vanadium, X, niobium, Z and oxygen, relative to molybdenum,
wherein
$0.01 \leq a \leq 100$;
$0.01 \leq b \leq 100$;
$0.01 \leq c \leq 100$;
$0 d \leq 100$; and
n is a number determined by the valence requirements of the other elements present,
the process comprising providing an aqueous raw material mixture containing compounds of the component elements of the composition of the formula (I), and drying the aqueous raw material mixture, followed by calcination,
wherein, in the aqueous raw material mixture, at least a part of the niobium compound as one of the compounds of the component elements is present in the form of a complex thereof with a complexing agent comprising a compound having a hydroxyl group bonded to an oxygen atom or a carbon atom.

For easy understanding of the present invention, the essential features and various preferred embodiments of the present invention are enumerated below.

1. A process for producing an oxide catalyst for use in a catalytic oxidation or ammoxidation of propane or isobutane in the gaseous phase, wherein the oxide catalyst comprises a composition represented by the following formula (I)

$$Mo_{1.0}V_aX_bNb_cZ_dO_n \qquad (I)$$

wherein:
X is at least one element selected from the group consisting of antimony and tellurium;
Z is at least one element selected from the group consisting of tungsten, chromium, titanium, aluminum, tantalum, zirconium, hafnium, manganese, rhenium, iron, ruthenium, cobalt, rhodium, nickel, palladium, platinum, zinc, boron, gallium, indium, germanium, tin, phosphorus, lead, bismuth, yttrium, rare earth elements and alkaline earth metals; and a, b, c, d, and n are, respectively, the atomic ratios of vanadium, X, niobium, Z and oxygen, relative to molybdenum,
wherein
$0.01 \leq a \leq 100$;
$0.01 \leq b \leq 100$;
$0.01 \leq c \leq 100$;
$0 \leq d \leq 100$ and
n is a number determined by the valence requirements of the other elements present, the process comprising providing an aqueous raw material mixture containing compounds of the component elements of the composition of the formula (I), and drying the aqueous raw material mixture, followed by calcination, wherein, in the aqueous raw material mixture, at least a part of the niobium compound as one of the compounds of the component elements is present in the form of a complex thereof with a complexing agent comprising a compound having a hydroxyl group bonded to an oxygen atom or a carbon atom.

2. The process according to item 1 above, wherein the aqueous raw material mixture has a complex formation ratio (R) of 20 mole % or more, the complex formation ratio (R) being defined by the following formula (II):

$$R(\text{mole \%}) = ((S1-S2)/(S3-S2)) \times 100 \quad \text{(II)}$$

wherein S1 represents the molar amount of the water-soluble niobium atoms in the aqueous raw material mixture, S2 represents the molar amount of the water-soluble niobium atoms which are not ascribed to the formation of the complex, and S3 represents the total molar amount of water-soluble niobium atoms and water-insoluble niobium atoms in the aqueous raw material mixture.

3. The process according to item 1 or 2 above, wherein the niobium compound is a niobium dicarboxylate.

4. The process according to item 3 above, wherein the niobium dicarboxylate is a compound which is formed by dissolving niobic acid in an aqueous dicarboxylic acid solution.

5. The process according to any one of items 1 to 4 above, wherein the complexing agent comprises at least one compound selected from the group consisting of hydrogen peroxide and a monooxypolycarboxylic acid.

6. The process according to item 4 or 5 above, wherein the aqueous raw material mixture is obtained by a process comprising:

dissolving niobic acid in an aqueous dicarboxylic acid solution to obtain an aqueous niobium dicarboxylate solution, mixing the obtained aqueous niobium dicarboxylate solution with the complexing agent or an aqueous solution of the complexing agent to obtain an aqueous niobium dicarboxylate/complexing agent solution, and mixing the obtained aqueous niobium dicarboxylate/complexing agent solution with a single aqueous mixture or two or more aqueous mixtures containing compounds of the component elements other than niobium to thereby obtain the aqueous raw material mixture.

7. The process according to item 4 or 5 above, wherein the aqueous raw material mixture is obtained by a process comprising:

mixing the complexing agent or an aqueous solution of the complexing agent with a single aqueous mixture or two or more aqueous mixtures containing compounds of the component elements other than niobium to obtain a complexing agent-containing aqueous non-niobium element compound mixture, and mixing the obtained complexing agent-containing aqueous non-niobium element compound mixture with an aqueous niobium dicarboxylate solution obtained by dissolving niobic acid in an aqueous dicarboxylic acid solution, to thereby obtain the aqueous raw material mixture.

8. The process according to any one of items 1 to 7 above, wherein the complexing agent is hydrogen peroxide.

9. The process according to any one of items 3 to 8 above, wherein the dicarboxylic acid is oxalic acid.

10. The process according to any one of items 1 to 9 above, wherein the aqueous raw material mixture further contains a source of silica in an amount such that the oxide catalyst further comprises a silica carrier having supported thereon the oxide catalyst, wherein the silica carrier is present in an amount of from 20 to 60% by weight, based on the total weight of the oxide catalyst and the silica carrier.

11. A process for producing acrylonitrile or methacrylonitrile, comprising reacting propane or isobutane with ammonia and molecular oxygen in the gaseous phase in the presence of the oxide catalyst produced by the process of any one of items 1 to 10 above.

12. A process for producing acrylic acid or methacrylic acid, comprising reacting propane or isobutane with molecular oxygen in the gaseous phase in the presence of the oxide catalyst produced by the process of any one of items 1 to 10 above.

The oxide catalyst obtained by the process of the present invention comprises a composition represented by the following formula (I)

$$Mo_{1.0}V_aX_bNb_cZ_dO_n \quad \text{(I)}$$

wherein:
X is at least one element selected from the group consisting of antimony and tellurium;
Z is at least one element selected from the group consisting of tungsten, chromium, titanium, aluminum, tantalum, zirconium, hafnium, manganese, rhenium, iron, ruthenium, cobalt, rhodium, nickel, palladium, platinum, zinc, boron, gallium, indium, germanium, tin, phosphorus, lead, bismuth, yttrium, rare earth elements and alkaline earth metals, and is preferably at least one element selected from the group consisting of tungsten, tin, titanium, gallium, germanium, aluminum and iron; and a, b, c, d, and n are, respectively, the atomic ratios of vanadium, X, niobium, Z and oxygen, relative to molybdenum,
wherein
$0.01 \leq a \leq 100$, preferably $0.1 \leq a \leq 1$, more preferably $0.2 \leq a \leq 0.4$;
$0.01 \leq b \leq 100$, preferably $0.01 \leq b \leq 0.6$, more preferably $0.1 \leq b \leq 0.3$;
$0.01 \leq c \leq 100$, preferably $0.01 \leq c \leq 0.3$, more preferably $0.03 \leq c \leq 0.2$;
$0 \leq d \leq 100$ preferably $0 \leq d \leq 1$, more preferably $0.01 \leq d \leq 0.3$; and
n is a number determined by the valence requirements of the other elements present.

The process of the present invention for producing an oxide catalyst comprises the following steps: a step for providing an aqueous raw material mixture, a step for drying the aqueous raw material mixture, and a step for calcining the dried raw material mixture. The characteristic feature of the process of the present invention resides in that, in the aqueous raw material mixture, at least a part of the niobium compound as one of the compounds of the component elements is present in the form of a complex thereof with a complexing agent comprising a compound having a hydroxyl group bonded to an oxygen atom or a carbon atom. The aqueous raw material mixture containing the above-mentioned specific complex is produced in the step for providing the aqueous raw material mixture. The aqueous raw material mixture is a liquid containing all component elements of the catalyst.

In the present invention, the complex which is formed between at least a part of the niobium compound and the specific complexing agent is a complex which is formed when an aqueous niobium compound solution and the complexing agent or an aqueous complexing agent solution are mixed together; a complex which is formed when a niobium compound and an aqueous complexing agent solution are mixed together; or a complex which is formed when a niobium compound and the complexing agent are simultaneously added to water to thereby dissolve them and mix them together in the water.

The complexing agent used in the present invention is a compound having a hydroxyl group bonded to an oxygen atom or a carbon atom (hereinafter, the compound is frequently referred to simply as "hydroxyl group-containing compounds". The hydroxyl group-containing compound used as the complexing agent has a molecular structure wherein a hydroxyl group (—OH) is bonded to an oxygen atom or a carbon atom. The "OH" in a carboxyl group (—COOH) is not a hydroxyl group, so that a compound containing only a carboxyl group is not a hydroxyl group-containing compound used as a complexing agent in the present invention.

Examples of niobium compounds used in the present invention include niobic acid, $NbCl_5$, $NbCl_3$, $Nb(OC_2H_5)_5$ and niobium oxalate. An example of an aqueous niobium compound solution is an aqueous niobium dicarboxylate solution which is obtained by dissolving niobic acid in an aqueous dicarboxylic acid solution. It is preferred to use an aqueous niobium dicarboxylate solution which is obtained by dissolving niobic acid in an aqueous dicarboxylic acid solution. As a dicarboxylic acid, oxalic acid is preferred. There are known several types of niobium oxalates; specifically, there are known a compound in which two oxalic acid molecules are coordinated to one niobium atom; a compound in which three oxalic acid molecules are coordinated to one niobium atom; and a compound in which five oxalic acid molecules are coordinated to one niobium atom. In the present invention, niobium oxalate may be any of the above-mentioned compounds.

It is preferred that the aqueous raw material mixture has a complex formation ratio (R) of from 20 to 100 mole %, more advantageously from 40 to 100 mole %, most advantageously from 90 to 100 mole %, wherein the complex formation ratio is defined by the following formula (II):

$$R(\text{mole \%}) = ((S1-S2)/(S3-S2)) \times 100 \quad \text{(II)}$$

wherein S1 represents the molar amount of the water-soluble niobium atoms in the aqueous raw material mixture, S2 represents the molar amount of the water-soluble niobium atoms which are not ascribed to the formation of the complex, and S3 represents the total molar amount of water-soluble niobium atoms and water-insoluble niobium atoms in the aqueous raw material mixture.

The above-mentioned complex formation ratio (R) is an index of the degree of formation of the above-mentioned complex of the niobium compound with the complexing agent in the aqueous raw material mixture, which complex is stable and does not precipitate in the aqueous raw material mixture. By virtue of the presence of the above-mentioned complex in the aqueous raw material mixture used in the process of the present invention for producing an oxide catalyst, the produced oxide catalyst exhibits excellent performance (in respect of selectivity, yield and space time yield) in a catalytic ammoxidation or oxidation of propane or isobutane in the gaseous phase for producing (meth) acrylonitrile or (meth)acrylic acid. However, if the amount of the above-mentioned complex in the aqueous raw material mixture is too small, wherein the complex formation ratio (R) does not reach 20 mole %, the degree of the improvement in the performance of the catalyst produced using such an aqueous raw material mixture is not so high. Further, it is likely that precipitation of niobium compounds cannot be satisfactorily suppressed, so that the efficiency in the step for producing the aqueous raw material mixture cannot be satisfactorily improved.

The molar amount (S1) of the water-soluble Nb atoms in the aqueous raw material mixture is the molar amount of all of the water-soluble Nb atoms present in an aqueous solution phase of the aqueous raw material mixture. This molar amount (S1) is obtained by a method comprising separating the aqueous raw material mixture into an aqueous solution phase and a precipitate phase by filtration, centrifugation or the like, and determining the amount of the Nb atoms in the aqueous solution phase by ICP emission spectroscopic analysis, atomic absorption spectrometry or the like.

The molar amount (S2) of the water-soluble Nb atoms which are not ascribed to the formation of the complex is obtained by a method comprising preparing the below-described reference sample of an aqueous raw material mixture, separating the reference sample of an aqueous raw material mixture into an aqueous solution phase and a precipitate phase by filtration, centrifugation or the like, and determining the amount of the Nb atoms in the aqueous solution phase by ICP emission spectroscopic analysis, atomic absorption spectrometry or the like. The reference sample of an aqueous raw material mixture is prepared by substantially the same procedure (in respect of the materials used and amounts thereof, the mixing order of the materials, the temperature conditions and the like) as in the production of the above-mentioned aqueous raw material mixture containing the complex, except that neither a complexing agent nor an aqueous solution of the complexing agent is added. When the determination of the molar amount (S2) is conducted with respect to an aqueous raw material mixture which has already been prepared, the determination can be conducted as follows. First, the presence of the complexing agent is confirmed by an appropriate analysis. Then, the aqueous raw material mixture is subjected to elemental analysis to conduct qualitative and quantitative determination of the components (including the complexing agent) which are contained in the aqueous raw material mixture. Based on the results of the elemental analysis, a referential sample, which has the same composition as the aqueous raw material mixture except that no complex is present, is prepared, and the determination of the molar amount (S2) is conducted by the same procedure as mentioned above.

As the total molar amount (S3) of water-soluble niobium atoms and water-insoluble niobium atoms in the aqueous raw material mixture, either of the following amount or sum can be used: the amount of the niobium atoms contained in the niobium compound used to obtain the aqueous raw material mixture, or the sum of the amount of the Nb atoms in the aqueous solution phase and the amount of the Nb atoms in the precipitate phase.

In general, the precipitation of the niobium compound in the aqueous raw material mixture completes about 15 minutes after the production of the aqueous raw material mixture. In view of this, in the present invention, the measurement of the complex formation ratio (R) is conducted 30 minutes after the production of the aqueous raw material mixture.

As can be seen from formula (II) defining the complex formation ratio (R), the larger the value of R, the smaller the solids content of the aqueous raw material mixture.

With respect to the process for producing an aqueous raw material mixture containing a complex which has been formed between the niobium compound and the complexing agent (i.e., the hydroxyl group-containing compound), there is no particular limitation as long as the complex can be formed. As preferred processes for producing the aqueous raw material mixture, there can be mentioned the following processes (a) and (b).

Process (a): A process which comprises:
  dissolving niobic acid in an aqueous dicarboxylic acid solution to obtain an aqueous niobium dicarboxylate solution,
  mixing the obtained aqueous niobium dicarboxylate solution with the complexing agent or an aqueous solution of the complexing agent to obtain an aqueous niobium dicarboxylate/complexing agent solution, and
  mixing the obtained aqueous niobium dicarboxylate/complexing agent solution with a single aqueous mixture or two or more aqueous mixtures containing compounds of the component elements other than niobium to thereby obtain the aqueous raw material mixture.

Process (b): A process which comprises:
  mixing the complexing agent or an aqueous solution of the complexing agent with a single aqueous mixture or two or more aqueous mixtures containing compounds of the component elements other than niobium to obtain a complexing agent-containing aqueous non-niobium element compound mixture, and
  mixing the obtained complexing agent-containing aqueous non-niobium element compound mixture with an aqueous niobium dicarboxylate solution obtained by dissolving niobic acid in an aqueous dicarboxylic acid solution, to thereby obtain the aqueous raw material mixture.

In process (a), a complex between the niobium compound and the complexing agent is formed before the addition of the non-niobium element compounds. In process (b), when two or more aqueous mixtures containing the non-niobium element compounds are used, wherein each aqueous mixture contains a part of the non-niobium element compounds and all aqueous mixtures collectively contain all of the non-niobium element compounds, it is possible that the two or more aqueous mixtures are used in an appropriate order so that only the final aqueous raw material mixture contains all of the non-niobium element compounds. Therefore, in process (b), when the complexing agent-containing aqueous non-niobium element compound mixture contains only a part of the non-niobium element compounds, the desired aqueous raw material mixture can be obtained by mixing together such complexing agent-containing aqueous non-niobium element compound mixture, an aqueous niobium dicarboxylate solution and one or more aqueous mixtures containing the remainder of the non-niobium element compounds, in an appropriate order.

Of the above-mentioned processes (a) and (b), more preferred is process (a).

The hydroxyl group-containing compound (that is, a compound having a hydroxyl group bonded to an oxygen atom or a carbon atom) used as the complexing agent is preferably at least one compound selected from the group consisting of hydrogen peroxide and a monooxypolycarboxylic acid. A monooxypolycarboxylic acid is a compound having one hydroxyl group and two or more carboxyl groups. Specific examples of monooxypolycarboxylic acids include tartronic acid, methyltartronic acid, ethyltartronic acid, n-propyltartronic acid, isopropyltartronic acid, oxymethylmalonic acid, oxyisopropylmalonic acid, ethyloxymethylmalonic acid, DL-malic acid, L-malic acid, D-malic acid, α-methylmalic acid, α-oxy-α'-methylsuccinic acid, α-oxy-α',α'-dimethylsuccinic acid, α-oxy-α,α'-dimethylsuccinic acid, α-oxy-α'-ethylsuccinic acid, α-oxy-α'-methyl-α-ethylsuccinic acid, trimethylmalic acid, α-oxyglutaric acid, β-oxyglutaric acid, dicrotalic acid, β-oxy-α,α-dimethylglutaric acid, β-oxy-α,α,γ-trimethylglutaric acid, β-oxy-α,α,β-trimethylglutaric acid, α-oxyadipic acid, α-methyl-α-oxyadipic acid, α-oxysuberic acid, α-oxysebacic acid, 2-oxy-2-octyltetradecanoic diacid, citric acid, isocitric acid, 4-oxypentane-1,3,4-tricaroboxylic acid and norcaperatic acid. Of these, citric acid, DL-malic acid, L-malic acid and D-malic acid are preferred.

Hydrogen peroxide is more preferred.

The molar ratio of the complexing agent to niobium (complexing agent/niobium molar ratio) in the aqueous raw material mixture is preferably in the range of from 0.2 to 10. When the complexing agent/niobium molar ratio is less than 0.2, it is possible that the obtained catalyst provides only a small improvement in the selectivity for, the yield of and the space time yield of (meth)acrylonitrile or (meth)acrylic acid. In addition, it is also possible that the precipitation of the niobium compound becomes large, so that only a small improvement can be obtained in the operation efficiency of the production of the aqueous raw material mixture. On the other hand, when the complexing agent/niobium molar ratio is more than 10, it is possible that the obtained catalyst causes a lowering of the selectivity for, the yield of and the space time yield of (meth)acrylonitrile or (meth)acrylic acid.

Hereinbelow, an explanation is made with respect to the process for producing the aqueous raw material mixture, taking as an example the case wherein the complexing agent is hydrogen peroxide.

The molar ratio of hydrogen peroxide to niobium (hydrogen peroxide/niobium molar ratio) is preferably from 0.2 to 10, more preferably from 0.4 to 8, most preferably from 2 to 6.

The hydrogen peroxide/niobium molar ratio is defined as follows. With respect to the compounds (raw material compounds) of the component elements in the composition of formula (1) (namely, molybdenum, vanadium, at least one element selected from the group consisting of the two elements of antimony and tellurium, niobium and optional Z element), when all of the component elements in the compounds respectively have oxidation numbers which are the same as the maximum oxidation numbers thereof, the hydrogen peroxide/niobium molar ratio is defined as the molar ratio of hydrogen peroxide used for preparing the aqueous raw material mixture to the niobium atoms contained in the aqueous raw material mixture. The maximum oxidation numbers of the essential component elements are as follows: molybdenum has a maximum oxidation number of 6; vanadium has a maximum oxidation number of 5, antimony has a maximum oxidation number of 5; tellurium has a maximum oxidation number of 6; and niobium has a maximum oxidation number of 5. With respect to the optional Z elements, the maximum oxidation numbers are as follows: tungsten has a maximum oxidation number of 6; chromium has a maximum oxidation number of 6; titanium has a maximum oxidation number of 4; aluminum has a maximum oxidation number of 3; tantalum has a maximum oxidation number of 5; zirconium has a maximum oxidation number of 4; hafnium has a maximum oxidation number of 4; manganese has a maximum oxidation number of 7; rhenium has a maximum oxidation number of 7; iron has a maximum oxidation number of 3, ruthenium has a maximum oxidation number of 4; cobalt has a maximum oxidation number of 3; rhodium has a maximum oxidation number of 4, nickel has a maximum oxidation number of 3; palladium has a maximum oxidation number of 4; platinum has a maximum oxidation number of 4; zinc has a maximum oxidation number of 2; boron has a maximum oxidation number of 3; gallium has a maximum oxidation number of 3; indium has a maximum oxidation number of 3; germanium has a maximum oxidation number of 4; tin has a maximum oxidation number of 4; phosphorus has a maximum oxidation number of 5; lead has a maximum oxidation number of 4; bismuth has a maximum oxidation number of 5; yttrium has a maximum oxidation number of 3; cerium has a maximum oxidation number of 4; and each of rare earth elements other than cerium has a maximum oxidation number of 3.

On the other hand, when the oxidation number of a component element contained in a compound thereof used as a raw material compound is smaller than the maximum oxidation number of the component element, the molar amount of hydrogen peroxide used as the complexing agent is defined as a number obtained by making the following subtraction: "the molar amount of hydrogen peroxide used for preparing the aqueous raw material mixture" minus "the total molar amount of hydrogen peroxide values necessary for increasing the non-maximum oxidation number of the component element up to the maximum oxidation number thereof". When a plurality of component elements respectively have oxidation numbers smaller than the maximum oxidation numbers thereof, the molar amount of hydrogen peroxide used as the complexing agent is determined as follows. First, the total molar amount of hydrogen peroxide values necessary for increasing the non-maximum oxidation numbers of the component elements respectively up to the maximum oxidation numbers thereof is determined, and the determined amount is subtracted from the molar amount of hydrogen peroxide used for preparing the aqueous raw material mixture. The molar amount of hydrogen peroxide necessary for increasing the non-maximum oxidation number of a component element up to the maximum oxidation number thereof is defined by the following formula:

$$(n-p) \times q/2$$

wherein:
n is the maximum oxidation number of the component element,
p is the oxidation number of the component element, and
q is the molar amount of the component element.

Hereinbelow, a detailed explanation is made with respect to the processes (a) and (b) for producing the aqueous raw material mixture, taking as an example the case where the complexing agent is hydrogen peroxide.

First, the process (a) is explained below in detail.

In process (a), niobic acid is dissolved in an aqueous dicarboxylic acid solution to obtain an aqueous niobium dicarboxylate solution having a niobium concentration of 0.01 to 2 mol/kg (preferably 0.1 to 0.8 mol/kg), and the obtained aqueous niobium dicarboxylate solution is mixed with 0.01 to 30 wt % aqueous hydrogen peroxide (preferably 0.1 to 10 wt % aqueous hydrogen peroxide) to thereby obtain an aqueous niobium-hydrogen peroxide solution. Then, the obtained aqueous niobium-hydrogen peroxide solution is mixed with a single aqueous mixture or two or more aqueous mixtures containing compounds of the component elements other than niobium (total concentration of the component elements other than niobium: 0.01 to 10 mol/kg, preferably 0.1 to 3 mol/kg), to thereby obtain the aqueous raw material mixture. It is preferred that the temperatures of the aqueous niobium-hydrogen peroxide solution and the above-mentioned single aqueous mixture or two or more aqueous mixtures are maintained within the range of from 1 to 65° C., preferably from 5 to 50° C. When the temperatures of these liquids are higher than 65° C., hydrogen peroxide is likely to be decomposed. On the other hand, when the temperatures of these liquids are lower than 1° C., they are likely to become frozen. Further, it is also preferred that the temperature of the obtained aqueous raw material mixture is maintained within the range of from 1 to 65° C.

As mentioned above, as a dicarboxylic acid used in the present invention, oxalic acid is preferred. The dicarboxylic acid/niobium molar ratio used in dissolving niobic acid in an aqueous dicarboxylic acid solution is from 1 to 10, preferably from 2 to 6, and more preferably from 2 to 4. When the dicarboxylic acid/niobium molar ratio is less than 1 or greater than 10, the obtained catalyst causes a lowering of the selectivity for (meth)acrylonitrile or (meth)acrylic acid.

When the single aqueous mixture containing the non-niobium element compounds contains all of the component elements other than niobium, the desired aqueous raw material mixture can be obtained by mixing the above-mentioned aqueous niobium-hydrogen peroxide solution and the single aqueous mixture containing the non-niobium element compounds. When two or more aqueous mixtures containing the non-niobium element compounds are used, wherein each aqueous mixture contains a part of the non-niobium element compounds and all aqueous mixtures collectively contain all of the non-niobium element compounds, the desired aqueous raw material mixture can be obtained by mixing the aqueous niobium-hydrogen peroxide solution and the two or more aqueous mixtures in an appropriate order.

The process (b) is explained below in detail.

In process (b), a single aqueous mixture or two or more aqueous mixtures containing compounds of the component elements other than niobium (total concentration of the component elements other than niobium: 0.01 to 10 mol/kg, preferably 0.1 to 3 mol/kg) are mixed with 0.01 to 30 wt % aqueous hydrogen peroxide (preferably 0.1 to 10 wt % aqueous hydrogen peroxide) to obtain a hydrogen peroxide-containing aqueous non-niobium element compound mixture. On the other hand, niobic acid is dissolved in an aqueous dicarboxylic acid solution to obtain an aqueous niobium dicarboxylate solution having a niobium concentration of 0.01 to 2 mol/kg (preferably 0.1 to 0.8 mol/kg), and the obtained aqueous niobium dicarboxylate solution is mixed with the above-obtained hydrogen peroxide-containing aqueous non-niobium element compound mixture to thereby obtain the aqueous raw material mixture.

When the single aqueous mixture containing the non-niobium element compounds contains all of the component elements other than niobium, the desired aqueous raw material mixture can be obtained by mixing the single aqueous mixture containing the non-niobium element compounds with aqueous hydrogen peroxide to obtain a hydrogen peroxide-containing aqueous non-niobium element compound mixture, and, then, mixing the obtained hydrogen peroxide-containing aqueous non-niobium element compound mixture with an aqueous niobium dicarboxylate solution obtained by dissolving niobic acid in an aqueous dicarboxylic acid solution. When two or more aqueous mixtures containing the non-niobium element compounds are used, wherein each aqueous mixture contains a part of the non-niobium element compounds and all aqueous mixtures collectively contain all of the non-niobium element compounds, the desired aqueous raw material mixture can be obtained by mixing an aqueous mixture containing a part of the non-niobium element compounds with aqueous hydrogen peroxide to obtain a hydrogen peroxide-containing aqueous non-niobium element compound mixture, and, then, mixing the obtained hydrogen peroxide-containing aqueous non-niobium element compound mixture with an aqueous niobium dicarboxylate solution (obtained by dissolving niobic acid in an aqueous dicarboxylic acid solution) and one or more aqueous mixtures containing the remainder of the non-niobium element compounds in an appropriate order.

It is preferred that the temperatures of the above-mentioned single aqueous mixture or two or more aqueous mixtures and the aqueous solutions are maintained within the range of from 1 to 60° C., preferably from 5 to 50° C., more preferably from 10 to 40° C. When the temperatures of these liquids are higher than 60° C., hydrogen peroxide is likely to be decomposed. On the other hand, when the temperatures of these liquids are lower than 1° C., they are likely to become frozen. Further, it is also preferred that the temperature of the obtained aqueous raw material mixture is maintained within the range of from 1 to 65° C.

As a dicarboxylic acid used in the present invention, oxalic acid is preferred. The dicarboxylic acid/niobium molar ratio used in dissolving niobic acid in an aqueous dicarboxylic acid solution is from 1 to 10, preferably from 2 to 6, and more preferably from 2 to 4. When the dicarboxylic acid/niobium molar ratio is less than 1 or greater than 10, the obtained catalyst causes a lowering of the selectivity for (meth)acrylonitrile or (meth)acrylic acid.

Process (a) can be performed in a broader temperature range than process (b), so that process (a) is superior to process (b) in operability.

Hereinbelow, a detailed explanation is made with respect to the processes (a) and (b) for producing the aqueous raw material mixture, taking as an example the case wherein the comlexing agent is a monooxypolycarboxylic acid.

First, the process (a) is explained in detail below

In process (a), niobic acid is dissolved in an aqueous dicarboxylic acid solution to obtain an aqueous niobium dicarboxylate solution having a niobium concentration of 0.01 to 2 mol/kg (preferably 0.1 to 0.8 mol/kg), and the obtained aqueous niobium dicarboxylate solution is mixed with a monooxypolycarboxylic acid to thereby obtain an aqueous niobium-monooxypolycarboxylic acid solution. (Alternatively, the aqueous niobium-monooxypolycarboxylic acid solution can also be obtained by dissolving niobic acid in an aqueous solution of a mixture of a dicarboxylic acid and a monooxypolycarboxylic acid.) Then, the obtained aqueous niobium-monooxypolycarboxylic acid solution is mixed with a single aqueous mixture or two or more aqueous mixtures containing compounds of the component elements other than niobium (total concentration of the component elements other than niobium: 0.01 to 10 mol/kg, preferably 0.1 to 3 mol/kg), to thereby obtain the aqueous raw material mixture. It is preferred that the temperatures of the aqueous niobium-monooxypolycarboxylic acid solution and the above-mentioned single aqueous mixture or two or more aqueous mixtures are maintained within the range of from 1 to 80° C., more advantageously from 5 to 70° C., most advantageously from 10 to 60° C. It is also preferred that the temperature of the obtained aqueous raw material mixture is maintained within the range of from 1 to 80° C.

As mentioned above, as a dicarboxylic acid used in the present invention, oxalic acid is preferred. The dicarboxylic acid/niobium molar ratio used in dissolving niobic acid in an aqueous dicarboxylic acid solution is from 1 to 10, preferably from 1 to 6, more preferably from 1 to 4. When the dicarboxylic acid/niobium molar ratio is less than 1 or greater than 10, the obtained oxide catalyst causes a lowering of the selectivity for (meth)acrylonitrile or (meth)acrylic acid.

When the single aqueous mixture containing the non-niobium element compounds contains all of the component elements other than niobium, the desired aqueous raw material mixture can be obtained by mixing the above-mentioned aqueous niobium-monooxypolycarboxylic acid solution and the single aqueous mixture containing the non-niobium element compounds. When two or more aqueous mixtures containing the non-niobium element compounds are used, wherein each aqueous mixture contains a part of the non-niobium element compounds and all aqueous mixtures collectively contain all of the non-niobium element compounds, the desired aqueous raw material mixture can be obtained by mixing the aqueous niobium-monooxypolycarboxylic acid solution and the two or more aqueous mixtures in an appropriate order.

The process (b) is explained below in detail.

In process (b), a single aqueous mixture or two or more aqueous mixtures containing compounds of the component elements other than niobium (total concentration of the component elements other than niobium: 0.01 to 10 mol/kg, preferably 0.1 to 3 mol/kg) are mixed with a monooxypolycarboxylic acid to obtain a monooxypolycarboxylic acid-containing aqueous non-niobium element compound mixture. On the other hand, niobic acid is dissolved in an aqueous dicarboxylic acid solution to obtain an aqueous niobium dicarboxylate solution having a niobium concentration of 0.01 to 2 mol/kg (preferably 0.1 to 0.8 mol/kg), and the obtained aqueous niobium dicarboxylate solution is mixed with the above-obtained monooxypolycarboxylic acid-containing aqueous non-niobium element compound mixture to thereby obtain the aqueous raw material mixture.

When the single aqueous mixture containing the non-niobium element compounds contains all of the component elements other than niobium, the desired aqueous raw material mixture can be obtained by mixing the single aqueous mixture containing the non-niobium element compounds with a monooxypolycarboxylic acid to obtain a monooxypolycarboxylic acid-containing aqueous non-niobium element compound mixture, and, then, mixing the obtained monooxypolycarboxylic acid-containing aqueous non-niobium element compound mixture with an aqueous niobium dicarboxylate solution obtained by dissolving niobic acid in an aqueous dicarboxylic acid solution. When two or more aqueous mixtures containing the non-niobium element compounds are used, wherein each aqueous mixture contains a part of the non-niobium element compounds and all aqueous mixtures collectively contain all of the non-niobium element compounds, the desired aqueous raw material mixture can be obtained by mixing an aqueous mixture containing a part of the non-niobium element compounds with a monooxypolycarboxylic acid to obtain a monooxypolycarboxylic acid-containing aqueous non-niobium element compound mixture, and, then, mixing the obtained monooxypolycarboxylic acid-containing aqueous non-niobium element compound mixture with an aqueous niobium dicarboxylate solution (obtained by dissolving niobic acid in an aqueous dicarboxylic acid solution) and one or more aqueous mixtures containing the remainder of the non-niobium element compounds in an appropriate order.

It is preferred that the temperatures of the above-mentioned single aqueous mixture or two or more aqueous mixtures and the aqueous solutions are maintained within the range of from 1 to 80° C, more advantageously from 5 to 70° C, most advantageously from 10 to 60° C. It is also preferred that the temperature of the obtained aqueous raw material mixture is maintained within the range of from 1 to 80° C.

As a dicarboxylic acid used in the present invention, oxalic acid is preferred. The dicarboxylic acid/niobium molar ratio used in dissolving niobic acid in an aqueous dicarboxylic acid solution is from 1 to 10, preferably from 1 to 6, more preferably from 1 to 4. When the dicarboxylic acid/niobium molar ratio is less than 1 or greater than 10, the obtained catalyst causes a lowering of the selectivity for (meth)acrylonitrile or (meth)acrylic acid.

As mentioned above, process (a) is preferred to process (b).

In the process of the present invention, it is preferred that the aqueous raw material mixture further contains a source of silica in an amount such that the oxide catalyst further comprises a silica carrier having supported thereon the oxide catalyst. It is preferred that the silica carrier is present in an amount of from 20 to 60% by weight, more advantageously from 25 to 55% by weight, based on the total weight of the oxide catalyst and the silica carrier.

The weight percentage of the silica carrier is defined by the following formula (III)

weight percentage of the silica carrier $$=(W2/(W1+W2))\times 100 \quad (III)$$

wherein W1 represents the weight of the oxide catalyst, which is calculated from the composition of the raw materials and the oxidation numbers of the component elements contained in the raw materials, and W2 represents the weight of the silica carrier in terms of $SiO_2$.

Next, an explanation is made below with respect to the compounds used in the process of the present invention as sources of the component elements of the oxide catalyst other than niobium, i.e., compounds used as sources of molybdenum, vanadium, at least one element X selected from the group consisting of antimony and tellurium, and the optional component element Z.

Examples of sources of molybdenum include ammonium heptamolybdate, molybdenum oxides, molybdic acid, molybdenum oxychlorides, molybdenum chlorides, molybdenum alkoxides and the like. Of these, ammonium heptamolybate is preferred.

Examples of sources of vanadium include ammonium metavanadate, vanadium (V) oxide, vanadium oxychlorides, and vanadium alkoxides. Of these, ammonium metavanadate and vanadium (V) oxide are preferred.

Examples of sources of antimony include antimony (III) oxide, antimony (IV) oxide, antimony(V) oxide, metantimonic acids (III), antimonic acids (V), ammonium antimonate (V), antimony (III) chloride, antimony (III) oxychloride, antimony (III) nitrate oxide, antimony alkoxides, organic acid salts of antimony, such as antimony tartrate, and metallic antimony. Of these, antimony (III) oxide is preferred.

Examples of sources of tellurium include telluric acid and metallic tellurium. Of these, telluric acid is preferred.

Examples of sources of Z elements include oxalic acid salts, hydroxides, oxides, nitrates, acetates, ammonium salts, carbonates and alkoxides of the Z elements.

When it is intended to use silica to obtain an oxide catalyst supported on a silica carrier, silica sol can be advantageously used as a source of silica. It is especially preferred to use a silica sol stabilized with ammonium ions.

Hereinbelow, a specific explanation is made with respect to the process of the present invention for producing an oxide catalyst. The process of the present invention comprises the following three steps: a step for providing an aqueous raw material mixture (i.e., step for preparing an aqueous raw material mixture), a step for drying the aqueous raw material mixture, and a step for calcining the resultant dried aqueous raw material mixture. These steps are explained below, referring to specific modes of the process of the present invention.

Aqueous Raw Material Mixture Preparation Step

With respect to the above-mentioned processes (a) and (b) for preparing the aqueous raw material mixture, specific modes thereof are described below. In each of the specific modes, an aqueous niobium oxalate solution obtained by dissolving a niobic acid in an aqueous oxalic acid solution is used as the aqueous solution of a niobium compound. Further, with respect to each of the specific modes of the processes (a) and (b), explanations are separately made below about the case where aqueous hydrogen peroxide is used as the complexing agent (i.e., the above-mentioned hydroxyl group-containing compound), and the case where citric acid (i.e., monoxypolycarboxylic acid) is used as the complexing agent.

In the Case where Aqueous Hydrogen Peroxide is Used as the Complexing Agent in the Above-Mentioned Process (a)

First, an explanation is made on the case where Te is used as the X element.

An aqueous niobium oxalate solution is prepared by dissolving a niobic acid in an aqueous oxalic acid solution. The oxalic acid/niobium molar ratio in the aqueous niobium oxalate solution is generally in the range of from 1 to 10, preferably from 2 to 6, most preferably from 2 to 4. To the obtained aqueous niobium oxalate solution is added aqueous hydrogen peroxide to obtain an aqueous niobium-hydrogen peroxide solution. The hydrogen peroxide/niobium molar ratio in the aqueous niobium-hydrogen peroxide solution is preferably in the range of from 0.2 to 10, more preferably from 0.4 to 8, most preferably from 2 to 6. It is preferred that the temperature of the obtained aqueous niobium-hydrogen peroxide solution is maintained at 65° C. or less, more advantageously 50° C. or less. The niobium concentration of the aqueous niobium-hydrogen peroxide solution is preferably 0.05 mol/kg or more, more preferably 0.15 mol/kg or more.

On the other hand, ammonium heptamolybdate, ammonium metavanadate and telluric acid are dissolved in water to obtain an aqueous solution. With respect to the obtained aqueous solution, the molybdenum concentration thereof is preferably 0.2 mol/kg or more, most preferably 0.5 mol/kg or more. This aqueous solution is mixed with the aqueous niobium-hydrogen peroxide solution to obtain an aqueous raw material mixture.

Next, an explanation is made on the case where Sb is used as the X element. An aqueous mixture containing ammonium heptamolybdate, ammonium metavanadate and antimony (III) oxide is subjected to a reaction, preferably, at 70 to 100° C. The resultant mixture containing molybdenum, vanadium and antimony is subjected to an oxidation by air or an oxidation in a liquid phase by using hydrogen peroxide or the like, to thereby obtain an aqueous solution. It is preferred that the oxidation is conducted to an extent wherein the change in color of the aqueous mixture from dark blue to orange or brown is visually observed. The molybdenum concentration of the resultant aqueous solution is preferably 0.2 mol/kg or more, more preferably 0.5 mol/kg or more. The obtained aqueous solution is cooled to 10 to 65° C., and the resultant solution is mixed with the aqueous niobium-hydrogen peroxide solution to obtain an aqueous raw material mixture.

Alternatively, to an aqueous solution having ammonium heptamolybdate dissolved therein are added antimony (III) oxide and aqueous hydrogen peroxide having a hydrogen peroxide concentration of 0.01 to 30% by weight (preferably 0.1 to 10% by weight), followed by stirring at 50 to 80° C. To the resultant aqueous solution is added ammonium metavanadate. The resultant aqueous solution is cooled to 10 to 65° C. and then, mixed with the aqueous niobium-hydrogen peroxide solution to obtain an aqueous raw material mixture.

In the Case where Aqueous Hydrogen Peroxide is used as the Complexing Agent in the Above-Mentioned Process (b)

First, an explanation is made on the case where Te is used as the X element.

An aqueous niobium oxalate solution is prepared by dissolving a niobic acid in an aqueous oxalic acid solution. The niobium concentration of the aqueous niobium oxalate solution is generally in the range of 0.05 mol/kg or more, more preferably 0.15 mol/kg or more.

On the other hand, ammonium heptamolybdate, ammonium metavanadate and telluric acid are dissolved in water to obtain an aqueous solution. Then, aqueous hydrogen peroxide is added to the obtained aqueous solution to thereby obtain an aqueous molybdenum-vanadium-tellurium solution containing hydrogen peroxide. With respect to the obtained aqueous solution, the molybdenum concentration thereof is preferably 0.2 mol/kg or more, more preferably 0.5 mol/kg or more. The amount of the aqueous hydrogen peroxide is selected such that the hydrogen peroxide/niobium molar ratio in the below-described aqueous raw material mixture is in the range from 0.2 to 10, more preferably from 0.4 to 8, most preferably from 2 to 6. The temperature of the aqueous molybdenum-vanadium-tellurium solution containing hydrogen peroxide is preferably in the range of from 1 to 60° C., more preferably from 5 to 50° C., most preferably from 10 to 40° C. This aqueous molybdenum-vanadium-tellurium solution containing hydrogen peroxide is mixed with the above-obtained aqueous niobium oxalate solution to thereby obtain an aqueous raw material mixture.

Next, an explanation is made on the case where Sb is used as the X element. An aqueous mixture containing ammonium heptamolybdate, ammonium metavanadate and antimony(III) oxide is subjected to a reaction, preferably, at 70 to 100° C. The resultant mixture containing molybdenum, vanadium and antimony is subjected to an oxidation by air or an oxidation in a liquid phase by using hydrogen peroxide or the like, to thereby obtain an aqueous solution. It is preferred that the oxidation is conducted to an extent wherein the change in color of the aqueous mixture from dark blue to orange or brown is visually observed. Alternatively, such an aqueous solution containing molybdenum, vanadium and antimony can be obtained as follows. To an aqueous solution having ammonium heptamolybdate dissolved therein are added antimony (III) oxide and aqueous hydrogen peroxide, followed by stirring at 50 to 80° C. To the resultant aqueous solution is added ammonium metavanadate, thereby obtaining an aqueous solution containing molybdenum, vanadium and antimony. The molybdenum concentration of the resultant aqueous solution containing molybdenum, vanadium and antimony is preferably 0.2 mol/kg or more, more preferably 0.5 mol/kg or more.

To the thus obtained aqueous solution containing molybdenum, vanadium and antimony is added aqueous hydrogen peroxide, to thereby obtain an aqueous molybdenum-vanadium-antimony solution containing hydrogen peroxide. The temperature of the aqueous solution containing molybdenum, vanadium and antimony at the time of addition of hydrogen peroxide is preferably in the range of from 1 to 60° C., more preferably from 5 to 50° C., most preferably from 10 to 40° C. The hydrogen peroxide is used in an amount wherein the hydrogen peroxide/niobium molar ratio in the below-described aqueous raw material mixture is preferably in the range of from 0.2 to 10, more preferably from 0.4 to 8, most preferably from 2 to 6.

In the case where the oxidation of the mixture containing molybdenum, vanadium and antimony (Sb) is conducted in a liquid phase at 1 to 40° C. by using aqueous hydrogen peroxide in an amount wherein the hydrogen peroxide/Sb molar ratio is preferably in the range of from 2.5 to 12.5, more preferably from 3 to 10, most preferably from 4 to 8, even if the addition of hydrogen peroxide as a complexing agent is omitted, the aqueous molybdenum-vanadium-antimony solution containing hydrogen peroxide can be obtained. The aqueous molybdenum-vanadium-antimony solution containing hydrogen peroxide is mixed with the above-obtained aqueous niobium oxalate solution to thereby obtain an aqueous raw material mixture.

As described above under Prior Art, in Unexamined Japanese Patent Application Laid-Open Specification Nos. 2000-70714, 11-285636 and 11-226408, it is described that a precipitation of a niobium compound has occurred during the production of an oxide catalyst. The reason for this is considered that the amount of hydrogen peroxide used is too small, so that most of the hydrogen peroxide is consumed in the oxidation of component elements each having a low oxidation number, or that the temperature of the aqueous raw material mixture containing component elements is high (i.e., at a temperature wherein a boiling of the raw material mixture occurs or at 70° C.), so that the hydrogen peroxide is decomposed.

When it is intended to produce an oxide catalyst supported on a silica carrier, a silica sol may be added at any time during the above-described procedures to thereby obtain a silica sol-containing aqueous raw material mixture.

When it is intended to produce an oxide catalyst containing the Z element which is an optional component, a compound containing the Z element may be added at any time during the above-described procedures to thereby obtain a Z element-containing aqueous raw material mixture.

In the Case where Citric Acid is Used as the Complexing Agent in the Above-Mentioned Process (a)

First, an explanation is made on the case where Te is used as the X element.

An aqueous niobium-oxalic acid-citric acid solution is prepared by either a method in which a niobic acid is dissolved in an aqueous oxalic acid solution, followed by addition of citric acid, or a method in which a niobic acid is dissolved in an aqueous solution of a mixture of oxalic acid and citric acid. With respect to the aqueous niobium-oxalic acid-citric acid solution, the oxalic acid/niobium molar ratio is generally in the range of from 1 to 10, preferably from 1 to 6, more preferably from 1 to 4, and the citric acid/niobium molar ratio is preferably 0.2 to 10, more preferably 0.4 to 6. It is preferred that the temperature of the obtained aqueous niobium-oxalic acid-citric acid solution is maintained at 1 to 80° C., more advantageously 1 to 60° C. The niobium concentration of the aqueous niobium-oxalic acid-citric acid solution is preferably 0.05 mol/kg or more, more preferably 0.15 mol/kg or more.

On the other hand, ammonium heptamolybdate, ammonium metavanadate and telluric acid are dissolved in water to obtain an aqueous solution. With respect to the obtained aqueous solution, the molybdenum concentration thereof is preferably 0.2 mol/kg or more, more preferably 0.5 mol/kg or more. This aqueous solution is mixed with the aqueous niobium-oxalic acid-citric acid solution to obtain an aqueous raw material mixture.

Next, an explanation is made on the case where Sb is used as the X element. An aqueous mixture containing ammonium heptamolybdate, ammonium metavanadate and antimony (III) oxide is subjected to a reaction, preferably, at 70 to 100° C. The resultant mixture containing molybdenum, vanadium and antimony is subjected to an oxidation by air or an oxidation in a liquid phase by using hydrogen peroxide or the like, to thereby obtain an aqueous solution. It is preferred that the oxidation is conducted to an extent wherein the change in color of the aqueous mixture from dark blue to orange or brown is visually observed. The molybdenum concentration of the resultant aqueous solution is preferably 0.2 mol/kg or more, most preferably 0.5 mol/kg or more. The obtained aqueous solution is cooled to 10 to 65° C., and the resultant solution is mixed with the aqueous niobium-oxalic acid-citric acid solution to obtain an aqueous raw material mixture.

Alternatively, to an aqueous solution having ammonium heptamolybdate dissolved therein are added antimony (III) oxide and aqueous hydrogen peroxide having a hydrogen peroxide concentration of 0.01 to 30% by weight (preferably 0.1 to 10% by weight), followed by stirring at 50 to 80° C. To the resultant aqueous solution is added ammonium metavanadate. The resultant aqueous solution is cooled to 10 to 65° C. and then, mixed with the aqueous niobium-oxalic acid-citric acid solution to obtain an aqueous raw material mixture.

In the Case where Citric Acid is Used as the Complexing Agent in the Above-Mentioned Process (b)

First, an explanation is made on the case where Te is used as the X element.

An aqueous niobium oxalate solution is prepared by dissolving a niobic acid in an aqueous oxalic acid solution. The niobium concentration of the aqueous niobium oxalate solution is generally in the range of 0.05 mol/kg or more, more preferably 0.15 mol/kg or more.

On the other hand, ammonium heptamolybdate, ammonium metavanadate and telluric acid are dissolved in water to obtain an aqueous solution. Then, citric acid is added to the obtained aqueous solution to thereby obtain an aqueous molybdenum-vanadium-tellurium solution containing citric acid. With respect to the obtained aqueous solution, the molybdenum concentration thereof is preferably 0.2 mol/kg or more, more preferably 0.5 mol/kg or more. The amount of the citric acid is appropriately selected such that the citric acid/niobium molar ratio in the below-described aqueous raw material mixture is in the range from 0.2 to 10, more preferably from 0.4 to 6. The temperature of the aqueous molybdenum-vanadium-tellurium solution containing citric acid is preferably in the range of from 1 to 80° C., more preferably from 5 to 70° C., most preferably from 10 to 60° C. This aqueous molybdenum-vanadium-tellurium solution containing citric acid is mixed with the above-obtained aqueous niobium oxalate solution to thereby obtain an aqueous raw material mixture.

Next, an explanation is made on the case where Sb is used as the X element. An aqueous mixture containing ammonium heptamolybdate, ammonium metavanadate and antimony(III) oxide is subjected to a reaction, preferably, at 70 to 100° C. The resultant mixture containing molybdenum, vanadium and antimony is subjected to an oxidation by air or an oxidation in a liquid phase by using hydrogen peroxide or the like, to thereby obtain an aqueous solution. It is preferred that the oxidation is conducted to an extent wherein the change in color of the aqueous mixture from dark blue to orange or brown is visually observed. Alternatively, such an aqueous solution containing molybdenum, vanadium and antimony can be obtained as follows. To an aqueous solution having ammonium heptamolybdate dissolved therein are added antimony (III) oxide and aqueous hydrogen peroxide, followed by stirring at 50 to 80° C. To the resultant aqueous solution is added ammonium metavanadate, thereby obtaining an aqueous solution containing molybdenum, vanadium and antimony. The molybdenum concentration of the resultant aqueous solution containing molybdenum, vanadium and antimony is preferably 0.2 mol/kg or more, more preferably 0.5 mol/kg or more.

To the thus obtained aqueous solution containing molybdenum, vanadium and antimony is added citric acid, to thereby obtain an aqueous molybdenum-vanadium-antimony solution containing citric acid. The temperature of the aqueous solution containing molybdenum, vanadium and antimony at the time of addition of citric acid is preferably in the range of from 1 to 80° C., more preferably from 5 to 70° C., most preferably from 10 to 60° C. The amount of the citric acid is appropriately selected such that the citric acid/niobium molar ratio in the below-described aqueous raw material mixture is in the range of from 0.2 to 10, more preferably from 0.4 to 6.

The thus obtained aqueous molybdenum-vanadium-antimony solution containing citric acid is mixed with the above-obtained aqueous niobium oxalate solution to thereby obtain an aqueous raw material mixture.

When it is intended to produce an oxide catalyst supported on a silica carrier, a silica sol may be added at any time during the above-described procedures to thereby obtain a silica sol-containing aqueous raw material mixture.

When it is intended to produce an oxide catalyst containing the Z element which is an optional component element Z, a compound containing the Z element may be added at any time during the above-described procedures to thereby obtain a Z element-containing aqueous raw material mixture.

Drying Step

The above-obtained aqueous raw material mixture is dried by spray drying or evaporation drying to thereby obtain a dried powder. The spray drying can be conducted by centrifugation, by the two-phase flow nozzle method or by the high pressure nozzle method. As a heat source for drying, it is preferred to use air which has been heated by steam, an electric heater and the like. It is preferred that the temperature of the heated air at an entrance to the dryer section thereof is from 150 to 300° C. The spray drying can be also conveniently conducted by spraying the aqueous raw material mixture onto an iron plate which has been heated to a temperature of 100 to 300° C.

Calcination Step

In the calcination step, the dried powder obtained in the drying step is calcined so as to obtain an oxide catalyst. The calcination can be conducted by using a kiln, such as a rotary kiln, a tunnel kiln, a muffle kiln or a fluidized-bed kiln. The calcination is conducted in an atmosphere of an inert gas, such as nitrogen gas which is substantially free of oxygen, or alternatively, in an atmosphere containing an oxidative gas (such as an oxygen-containing gas) in combination with a reductive gas (such as a gaseous organic compound (e.g., propane or isobutane) or gaseous ammonia). The calcination is preferably conducted in an atmosphere of an inert gas, such as nitrogen gas which is substantially free of oxygen, more preferably under a flow of an inert gas, at a temperature of 400 to 700° C., preferably 570 to 670° C. The time of calcination is generally 0.5 to 5 hours, preferably 1 to 3 hours. It is preferred that the oxygen concentration of the above-mentioned inert gas is 1000 ppm or less, more preferably 100 ppm or less as measured by gas chromatography or by means of a trace oxygen analyzer. The calcination can be conducted repeatedly. Prior to the calcination, the dried powder may be subjected to precalcination in an atmosphere of air or under a stream of air at 200 to 420° C., preferably 250 to 350° C. for 10 minutes to 5 hours. The catalyst obtained by calcination may be subjected to further calcination in an atmosphere of air at a temperature of from 200 to 400° C. for 5 minutes to 5 hours.

Ammoxidation and Oxidation of Propane or Isobutane in the Presence of the Oxide Catalyst The oxide catalyst produced in the above-mentioned manner can be used as a catalyst for producing (meth) acrylonitrile by ammoxidation of propane or isobutane in the gaseous phase. The oxide catalyst can also be used as a catalyst for producing (meth) acrylic acid by oxidation of propane or isobutane in the gaseous phase. The oxide catalyst is preferably used as a catalyst for producing (meth)acrylonitrile, more preferably used as a catalyst for producing acrylonitrile.

Propane or isobutane used for producing (meth)acrylic acid, and propane or isobutane and ammonia used for producing (meth)acrylonitrile need not be of a very high purity but may be of a commercial grade.

Examples of sources of molecular oxygen fed into the reaction system include air, oxygen-rich air, and pure oxygen. Further, such a source of molecular oxygen may be diluted with steam, helium, argon, carbon dioxide, nitrogen or the like.

In the case of an ammoxidation reaction in the gaseous phase, the molar ratio of ammonia to propane or isobutane for the ammoxidation is generally in the range of from 0.1 to 1.5, preferably from 0.2 to 1.2. The molar ratio of molecular oxygen to propane or isobutane used for the ammoxidation is generally in the range of from 0.2 to 6, preferably from 0.4 to 4.

In the case of an oxidation reaction in the gaseous phase, the molar ratio of molecular oxygen to propane or isobutane used for the oxidation is generally in the range of from 0.1 to 10, preferably from 0.1 to 5. It is preferred that steam is introduced into the reaction system. The molar ratio of steam to propane or isobutane used for the oxidation is generally in the range of from 0.1 to 70, preferably from 0.5 to 40.

In each of the ammoxidation reaction in the gaseous phase and the oxidation reaction in the gaseous phase, the reaction pressure is generally in the range of from 0.01 to 1 MPa, preferably from 0.1 to 0.3 Mpa, in terms of the absolute pressure.

In each of the ammoxidation reaction in the gaseous phase and the oxidation reaction in the gaseous phase, the reaction temperature is generally in the range of from 300 to 600° C., preferably from 380 to 470° C.

In each of the ammoxidation reaction in the gaseous phase and the oxidation reaction in the gaseous phase, the time of contact (contact time) between the gaseous feedstocks and the catalyst is generally in the range of from 0.1 to 30 (g·sec/ml), preferably from 0.5 to 10 (g·sec/ml). In the process of the present invention, the contact time is determined according to the following formula:

$$\text{Contact time (g} \cdot \text{sec/ml)} = \frac{W}{F} \times 60 \times \frac{273}{273+T} \times \frac{P+0.101}{0.101}$$

wherein:

W represents the weight (g) of the catalyst contained in the reactor;

F represents the flow rate (ml/min) of the gaseous feed stocks;

T represents the reaction temperature (° C.); and

P represents the reaction pressure (MPa) (gauge pressure).

Each of the ammoxidation reaction in the gaseous phase and the oxidation reaction in the gaseous phase can be conducted in a conventional reactor, such as a fixed bed reactor, a fluidized-bed reactor or a moving bed reactor, preferably in a fluidized-bed reactor. The reaction mode may be either a one pass mode or a recycling mode.

BEST MODE FOR CARRYING OUT THE INVENTION

Hereinbelow, the present invention will be described in more detail with reference to the following Examples and Comparative Examples, which should not be construed as limiting the scope of the present invention.

In the following Examples and Comparative Examples, the results of the oxidation or ammoxidation were evaluated in terms of the conversion (%) of propane, the selectivity (%) for acrylonitrile, the space time yield ($\mu$mole/ ((g·sec/ ml)·g)) of acrylonitrile, the selectivity (%) for acrylic acid and the space time yield ($\mu$mole/ ((g·sec/ml)·g)) of acrylic acid, which are, respectively, defined as follows:

$$\text{Conversion (\%) of propane} = \frac{\text{mole of propane reacted}}{\text{mole of propane fed}} \times 100$$

$$\frac{\text{Selectivity (\%)}}{\text{for acrylonitrile}} = \frac{\text{mole of acrylonitrile formed}}{\text{mole of propane reacted}} \times 100$$

$$\begin{array}{l}\text{Space time yield} \\ (\mu \text{ mole}/((\text{g} \cdot \sec/\text{ml}) \cdot \text{g})) = \\ \text{of acrylonitrile}\end{array} \frac{\mu \text{ mole of acrylonitrile formed}}{\text{Contact time (g} \cdot \sec/\text{ml}) \times \text{weight of catalyst (g)}}$$

$$\frac{\text{Selectivity (\%)}}{\text{for acrylic acid}} = \frac{\text{mole of acrylic acid formed}}{\text{mole of propane reacted}} \times 100$$

$$\begin{array}{l}\text{Space time yield} \\ (\mu \text{ mole}/((\text{g} \cdot \sec/\text{ml}) \cdot \text{g})) = \\ \text{of acrylic acid}\end{array} \frac{\mu \text{ mole of acrylic acid formed}}{\text{Contact time (g} \cdot \sec/\text{ml}) \times \text{weight of catalyst (g)}}$$

EXAMPLE 1

Preparation of a Catalyst

An oxide catalyst represented by the formula: $Mo_1V_{0.31}Sb_{0.20}Nb_{0.05}O_n/SiO_2$ (40% by weight) was prepared as follows.

To 1,000 g of water were added 250 g of ammonium heptamolybdate [$(NH_4)_6Mo_7O_{24} \cdot 4H_2O$], 51.3 g of ammonium metavanadate ($NH_4VO_3$) and 41.3 g of antimony (III) oxide ($Sb_2O_3$), and the resultant mixture was subjected to a reaction under reflux in an oil bath in the air at 100° C. for 2 hours, followed by cooling to 50° C. Subsequently, to the resultant reaction mixture was added 654 g of a silica sol having an $SiO_2$ content of 30% by weight, followed by stirring for 1 hour. Then, to the resultant mixture was further added 193 g of 5 wt % aqueous hydrogen peroxide, and the resultant mixture was stirred at 50° C. for 1 hour to effect an oxidation treatment, to thereby obtain an aqueous mixture ($a_1$). By the oxidation treatment, the color of the mixture changed from dark blue to brown.

On the other hand, to 120 g of water were added 12.4 g of niobic acid ($Nb_2O_5$ content: 76% by weight) and 24.1 g of oxalic acid dehydrate ($H_2C_2O_4 \cdot 2H_2O$), and the resultant mixture was heated at 60° C. while stirring to dissolve the niobic acid and oxalic acid dihydrate in the water, followed by cooling to 30° C., to thereby obtain an aqueous niobium-oxalic acid solution. To the obtained aqueous niobium-oxalic acid solution was added 96.3 g of 5 wt % aqueous hydrogen peroxide to thereby obtain an aqueous niobium-hydrogen peroxide solution.

The thus obtained aqueous niobium-hydrogen peroxide solution was added to the above-prepared aqueous mixture ($a_1$), and the resultant mixture was stirred at 50° C. for 30 minutes in the air, to thereby obtain an aqueous raw material mixture. 10 g of the aqueous raw material mixture was taken and subjected to filtration under pressure by means of a membrane filter (manufactured and sold by Advantec Toyo, Japan; PTFE; pore diameter: 0.2 μm; prior to use, the filter was immersed in ethanol and then washed with water), thereby separating rating the taken aqueous raw material mixture into an aqueous solution phase and a precipitate phase. The amount of the Nb atoms in the aqueous solution phase (i.e., the value of S1) was determined by ICP emission spectroscopic analysis (by means of emission spectrometer "Rigaku JY138 ULTRACE", manufactured and sold by Rigaku Corporation, Japan), and S1 was found to be 70.9 mmole. On the other hand, the above-described procedure for producing an aqueous raw material mixture was repeated, except that, instead of the 96.3 g of 5 wt % aqueous hydrogen peroxide, 91.5 g of water was added to an aqueous niobium-oxalic acid solution, to thereby obtain a reference sample of an aqueous raw material mixture. From the obtained reference sample of an aqueous raw material mixture, an aqueous solution phase was separated, and the amount of the Nb atoms in the aqueous solution phase (i.e., the value of S2) was determined by the same method as mentioned above. It was found that S2 was 3.7 mmole. From the amount of the niobium compound used, S3 was found to be 70.9 mmole. The complex formation ratio (R) was calculated from S1, S2 and S3, in accordance with the formula (II); it was found that R=100 mole % (R was obtained by calculating the formula: (70.9−3.7)/(70.9−3.7)×100). (S1, S2, S3 and R are as defined above, and this also applies to the subsequent Examples and Comparative Examples.)

The obtained aqueous raw material mixture was subjected to a spray drying by means of a centrifugation type spray-drying apparatus under conditions wherein the entrance and exit temperatures of the dryer of the spray-drying apparatus were 230° C. and 120° C., respectively, to thereby obtain a dried powder comprised of spherical particles. 100 g of the obtained dried powder was charged into a quartz container and calcined in a kiln at 630° C. for 2 hours under a flow of nitrogen gas at a flow rate of 600 ml/min while rotating the quartz container, to thereby obtain an oxide catalyst. The oxygen concentration of the nitrogen gas used for the calcination was determined by means of a trace oxygen analyzer (Model 306WA, manufactured and sold by Teledyne Analytical Instruments, U.S.A.), and it was found that the oxygen concentration of the nitrogen gas was 1 ppm. The composition of the oxide catalystz and the important conditions of the catalyst production process are shown in Table 1.

Ammoxidation of Propane 0.35 g of the obtained oxide catalyst (W=0.35 g) was charged into a fixed-bed type reaction tube having an inner diameter of 4 mm. A gaseous feedstock mixture having a molar ratio of propane:ammonia:oxygen:helium of 1:0.7:1.7:5.3 was fed into the reaction tube at a flow rate (F) of 7.0 (ml/min). The reaction temperature (T) was 420° C. and the reaction pressure (P) was 0 MPa in terms of the gauge pressure. The contact time between the oxide catalyst and the gaseous mixture of the feedstocks was 1.2 (g·sec/ml). The contact time was obtained by the following formula:

$$\text{Contact time} = \frac{W}{F} \times 60 \times \frac{273}{273+T} \times \frac{P+0.101}{0.101}$$

The produced gaseous reaction mixture was analyzed by means of an on-line gas chromatography apparatus. The results are shown in Table 1.

EXAMPLE 2

Preparation of a Catalyst

Preparation of an oxide catalyst was performed in substantially the same manner as in Example 1, except that the amount of 5 wt % aqueous hydrogen peroxide which was added to an aqueous niobium-oxalic acid solution was changed from 96.3 g to 48.2 g. The complex formation ratio (R) was determined in the same manner as in Example 1. It was found that S1=35.5 mmole, S2=3.6 mmole and S3=70.9 mmole, so that R was found to be 47 mole %. The composition of the oxide catalyst and the important conditions of the catalyst production process are shown in Table 1.

Ammoxidation of Propane

Using the obtained oxide catalyst, the ammoxidation reaction of propane was performed in substantially the same manner as in Example 1, except that the flow rate (F) of the gaseous feedstock mixture was changed to 5.2 (ml/min) and the contact time was changed to 1.6 (g·sec/ml). The results are shown in Table 1.

EXAMPLE 3

Preparation of a Catalyst

Preparation of an oxide catalyst was performed in substantially the same manner as in Example 1, except:

that, prior to the use of the aqueous mixture ($a_1$), the aqueous mixture ($a_1$) was cooled to 30° C. followed by the addition of 144 g of 5 wt % aqueous hydrogen peroxide, and that 5 wt % aqueous hydrogen peroxide was not added to the aqueous niobium-oxalic acid solution.

The complex formation ratio (R) was determined in the same manner as in Example 1. It was found that S1=70.9 mmole, S2=3.8 mmole and S3=70.9 mmole, so that R was found to be 100 mole %. The composition of the oxide catalyst and the important conditions of the catalyst production process are shown in Table 1.

Ammoxidation of Propane

Using the obtained oxide catalyst, the ammoxidation reaction of propane was performed in substantially the same manner as in Example 1, except that the flow rate (F) of the gaseous feedstock mixture was changed to 7.5 (ml/min) and the contact time was changed to 1.1 (g·sec/ml). The results are shown in Table 1.

COMPARATIVE EXAMPLE 1

Preparation of a Catalyst

Preparation of an oxide catalyst was performed in substantially the same manner as in Example 1, except that aqueous hydrogen peroxide was not added to an aqueous niobium-oxalic acid solution. The complex formation ratio (R) was determined in the same manner as in Example 1. It was found that S1=3.6 mmole, S2=3.6 mmole and S3=70.9 mmole, so that R was found to be 0 mole % (in this Comparative Example, S2=Si). The composition of the oxide catalyst and the important conditions of the catalyst production process are shown in Table 1.

Ammoxidation of Propane

Using the obtained oxide catalyst, the ammoxidation reaction of propane was performed in substantially the same manner as in Example 1, except that the flow rate (F) of the gaseous feedstock mixture was changed to 4.0 (ml/min) and the contact time was changed to 2.1 (g·sec/ml). The results are shown in Table 1.

COMPARATIVE EXAMPLE 2

Preparation of a Catalyst

Preparation of an oxide catalyst was performed in substantially the same manner as in Example 3, except that, prior to the use of aqueous mixture ($a_1$), the aqueous mixture ($a_1$) was heated to 70° C. followed by the addition of 144 g of 5 wt % aqueous hydrogen peroxide and stirring for 1 hour. The complex formation ratio (R) was determined in the same manner as in Example 1. It was found that S1=3.6 mmole and S3=70.9 mmole, so that R was found to be 0 mole %. The composition of the oxide catalyst and the important conditions of the catalyst production process are shown in Table Table 1 shows that, in Examples 1 to 3, the amount of the water-soluble Nb atoms (i.e., S1) was remarkably large, as compared to those in Comparative Examples 1 and 2.

Ammoxidation of Propane

Using the obtained oxide catalyst, the ammoxidation reaction of propane was performed in substantially the same manner as in Example 1, except that the flow rate (F) of the gaseous feedstock mixture was changed to 4.0 (ml/min) and the contact time was changed to 2.1 (g·sec/ml). The results are shown in Table 1.

EXAMPLE 4

Preparation of a Catalyst

An oxide catalyst represented by the formula: $Mo_1V_{0.31}Sb_{0.17}Nb_{0.05}O_n/SiO_2$(40% by weight) was prepared as follows.

250 g of ammonium heptamolybdate [$(NH_4)_6Mo_7O_{24}\cdot 4H_2O$] was dissolved in 1,000 g of water to obtain an aqueous solution. To the obtained aqueous solution were added 35.1 g of antimony (III) oxide ($Sb_2O_3$) and 164 g of 5 wt % aqueous hydrogen peroxide, followed by stirring at a temperature of 60 to 80° C. for 2 hours, to thereby obtain an aqueous solution. To the obtained aqueous solution was added 51.3 g of ammonium metavanadate ($NH_4VO_3$), followed by stirring for 15 minutes to thereby obtain an aqueous solution. The obtained aqueous solution was cooled to 50° C., and to the cooled aqueous solution was added 640 g of a silica sol having an $SiO_2$ content of 30% by weight, to thereby obtain an aqueous mixture ($a_2$).

On the other hand, to 120 g of water were added 12.4 g of niobic acid ($Nb_2O_5$ content: 76% by weight) and 24.1 g of oxalic acid dehydrate ($H_2C_2O_4\cdot 2H_2O$), and the resultant mixture was heated at 60° C. while stirring to dissolve the niobic acid and oxalic acid dihydrate in the water, followed by cooling to 30° C., to thereby obtain an aqueous niobium-oxalic acid solution. To the obtained aqueous niobium-oxalic acid solution was added 96.3 g of 5 wt % aqueous hydrogen peroxide to thereby obtain an aqueous niobium-hydrogen peroxide solution. The thus obtained aqueous niobium-hydrogen peroxide solution was added to the above-prepared aqueous mixture ($a_2$), and the resultant mixture was stirred at 50° C. for 30 minutes in the air, to thereby obtain an aqueous raw material mixture.

The complex formation ratio (R) was determined in the same manner as in Example 1. It was found that S1=70.9 mmole, S2=3.7 mmole and S3=70.9 mmole, so that R was found to be 100 mole %.

The obtained aqueous raw material mixture was subjected to a spray drying by means of a centrifugation type spray-drying apparatus under conditions wherein the entrance and exit temperatures of the dryer of the spray-drying apparatus were 230° C. and 120° C., respectively, to thereby obtain a dried powder comprised of spherical particles. 100 g of the obtained dried powder was charged into a quartz container and calcined in a kiln at 630° C. for 2 hours under a flow of nitrogen gas at a flow rate of 600 ml/min while rotating the quartz container, to thereby obtain an oxide catalyst. The composition of the oxide catalyst and the important conditions of the catalyst production process are shown in Table 1.

Ammoxidation of Propane

Using the obtained oxide catalyst an ammoxidation reaction was performed in substantially the same manner as in Example 1. The results are shown in Table 1.

COMPARATIVE EXAMPLE 3

Preparation of a Catalyst

Preparation of an oxide catalyst was performed in substantially the same manner as in Example 4, except that aqueous hydrogen peroxide was not added to an aqueous niobium-oxalic acid solution. The complex formation ratio (R) was determined in the same manner as in Example 1. It was found that S1=3.6 mmole, S2=3.6 mmole and S3=70.9 mmole, so that R was found to be 0 mole % (in this Comparative Example, S2=S1). The composition of the oxide catalyst and the important conditions of the catalyst production process are shown in Table 1.

Table 1 shows that, in Example 4, the amount of the water-soluble Nb atoms (i.e., S1) was remarkably large, as compared to that in Comparative Example 3.

Ammoxidation of Propane

Using the obtained oxide catalyst, the ammoxidation reaction of propane was performed in substantially the same manner as in Example 1, except that the flow rate (F) of the gaseous feedstock mixture was changed to 4.0 (ml/min) and the contact time was changed to 2.1 (g·sec/ml). The results are shown in Table 1.

EXAMPLE 5

Preparation of a Catalyst

An oxide catalyst represented by the formula: $Mo_1VO_{0.33}Te_{0.22}Nb_{0.11}O_n$ was prepared as follows.

To 160 g of water were added 39.0 g of ammonium heptamolybdate [$(NH_4)_6Mo_7O_{24}\cdot 4H_2O$], 8.53 g of ammonium metavanadate ($NH_4VO_3$) and 11.16 g of telluric acid ($H_6TeO_6$), and the resultant mixture was heated to 60° C. while stirring to dissolve these compounds in the water, followed by cooling to 30° C., to thereby obtain an aqueous mixture ($a_3$).

On the other hand, to 50 g of water were added 4.25 g of niobic acid ($Nb_2O_5$ content: 76% by weight) and 8.27 g of oxalic acid dehydrate ($H_2C_2O4.2H_2O$), and the resultant mixture was heated to 60° C. while stirring to dissolve the niobic acid and oxalic acid dihydrate in the water, followed by cooling to 30° C., to thereby obtain an aqueous niobium-oxalic acid solution. To the obtained aqueous niobium-oxalic acid solution was added 41.3 g of 5 wt % aqueous hydrogen peroxide to thereby obtain an aqueous niobium-hydrogen peroxide solution.

The thus obtained aqueous niobium-hydrogen peroxide solution was added to the above-prepared aqueous mixture ($a_3$), and the resultant mixture was stirred for 30 minutes, to thereby obtain an aqueous raw material mixture. The complex formation ratio (R) was determined in the same manner as in Example 1. It was found that S1=24.3 mmole, S2=0.8 mmole and S3=24.3 mmole, so that R was found to be 100 mole %.

The obtained aqueous raw material mixture was sprayed onto a Teflon-coated steel plate having a temperature of 140° C., to thereby obtain a dried powder. 25 g of the obtained dried powder was charged into a quartz tube having an inner diameter of 20 mm and calcined at 600° C. for 2 hours under a flow of nitrogen gas at a flow rate of 1,000 ml/mm to thereby obtain an oxide catalyst. The composition of the oxide catalyst and the important conditions of the catalyst production process are shown in Table 1.

Ammoxidation of Propane 0.30 g of the obtained oxide catalyst (W=0.30 g) was charged into a fixed-bed type reaction tube having an inner diameter of 4 mm. A gaseous feedstock mixture having a molar ratio of propane:ammonia:oxygen:helium of 1:1.2:3.0:14.8 was fed into the reaction tube at a flow rate (F) of 9.0 (ml/min). The reaction temperature (T) was 420° C., the reaction pressure (P) was 0 MPa in terms of the gauge pressure, and the contact time was 0.79 (g·sec/ml).

The produced gaseous reaction mixture was analyzed by means of an on-line gas chromatography apparatus. The results are shown in Table 1.

COMPARATIVE EXAMPLE 4

Preparation of a Catalyst

Preparation of an oxide catalyst was performed in substantially the same manner as in Example 5, except that aqueous hydrogen peroxide was not added to an aqueous niobium-oxalic acid solution. The complex formation ratio (R) was determined in the same manner as in Example 1. It was found that. S1=0.7 mmole, S2=0.7 mmole and S3=24.3 minnie, so that R was found to be 0 mole % (in this Comparative Example, S2=S1). The composition of the oxide catalyst and the important conditions of the catalyst production process are shown in Table 1.

Table 1 shows that, in Example 5, the amount of the water-soluble Nb atoms (i.e., S1) was remarkably large, as compared to that in Comparative Example 4.

Ammoxidation of Propane

Using the obtained oxide catalyst, the ammoxidation reaction of propane was performed in substantially the same manner as in Example 5, except that the flow rate (F) of the gaseous feedstock mixture was changed to 6.0 (ml/min) and the contact time was changed to 1.2 (g·sec/ml). The results are shown in Table 1.

EXAMPLE 6

Preparation of a Catalyst

An oxide catalyst represented by the formula: $Mo_1V_{0.33}Te_{0.22}Nb_{0.12}O_n/SiO_2$(30% by weight) was prepared as follows.

To 720 g of water were added 164.31 g of ammonium heptamolybdate [$(NH_4)_6Mo_7O_{24}\cdot 4H_2O$], 36.05 g of ammonium metavanadate ($NH_4VO_3$) and 47.01 g of telluric acid ($H_6TeO_6$), and the resultant mixture was heated to 60° C. while stirring to dissolve these compounds in the water, to thereby obtain an aqueous mixture ($a_4$).

On the other hand, to 170 g of water were added 19.53 g of niobic acid ($Nb_2O_5$ content: 76.6% by weight) and 38.0 g of oxalic acid dehydrate ($H_2C_2O_4.2H_2O$), and the resultant mixture was heated to 60° C. while stirring to dissolve the niobic acid and oxalic acid dehydrate in the water, followed by cooling to 30° C., to thereby obtain an aqueous niobium-oxalic acid solution. To the obtained aqueous niobium-oxalic acid solution was added 167.2 g of 5 wt % aqueous hydrogen peroxide to thereby obtain an aqueous niobium-hydrogen peroxide solution.

To the above-obtained aqueous mixture ($a_4$) was added 286 g of a silica sol having an $SiO_2$ content of 30% by weight while stirring, followed by cooling to 30° C. To the resultant mixture was added the above-prepared aqueous niobium-hydrogen peroxide solution to thereby obtain an aqueous raw material mixture.

The complex formation ratio (R) was determined in the same manner as in Example 1. It was found that S1=113 mmole, S2=3.9 mmole and S3=113 mmole, so that R was found to be 100 mole %.

The obtained aqueous raw material mixture was subjected to a spray drying by means of a centrifugation type spray-drying apparatus under conditions wherein the entrance and exit temperatures of the dryer of the spray-drying apparatus were 240° C. and 145° C., respectively, to thereby obtain a dried powder comprised of spherical particles. The obtained dried powder was pre-calcined at 240° C. for 2 hours in the air to thereby obtain a catalyst precursor. The obtained catalyst precursor was calcined under substantially the same calcination conditions as in Example 1, except that the calcination temperature was changed to 600° C., to thereby obtain an oxide catalyst. The composition of the oxide catalyst and the important conditions of the catalyst production process are shown in Table 1.

Ammoxidation of Propane 45 g of the obtained oxide catalyst was charged into a Vycor glass fluidized-bed reaction tube having an inner diameter of 25 mm. A gaseous feedstock mixture having a molar ratio of propane:ammonia:oxygen:helium of 1:1.2:3:12 was fed into the reaction tube at a flow rate of 450 (ml/min). The reaction temperature was 430° C., the reaction pressure was 0 MPa in terms of the gauge pressure, and the contact time was 2.3 (g·sec/ml). The produced gaseous reaction mixture was analyzed by means of an on-line gas chromatography apparatus. The results are shown in Table 1.

COMPARATIVE EXAMPLE 5

Preparation of a Catalyst

Preparation of an oxide catalyst was performed in substantially the same manner as in Example 6, except that aqueous hydrogen peroxide was not added to an aqueous niobium-oxalic acid solution. The complex formation ratio (R) was determined in the same manner as in Example 1. It was found that S1=3.4 mmole, S2=3.4 mmole and S3=113 mmole, so that R was found to be 0 mole % (in this Comparative Example, S2=81). The composition of the oxide catalyst and the important conditions of the catalyst production process are shown in Table 1.

Table 1 shows that, in Example 6, the amount of the water-soluble Nb atoms (i.e., S1) was remarkably large, as compared to that in Comparative Example 5.

Ammoxidation of Propane

Using the obtained oxide catalyst, the ammoxidation reaction of propane was performed in substantially the same manner as in Example 6, except that the flow rate (F) of the gaseous feedstock mixture was changed to 350 (ml/min) and the contact time was changed to 3.0 (g·sec/ml). The results are shown in Table 1.

EXAMPLE 7

Preparation of a Catalyst

An oxide catalyst represented by the formula: $Mo_1V_{0.28}Te_{0.23}Nb_{0.12}O_n/SiO_2$(23% by weight) was prepared as follows.

To 720 g of water were added 164.31 g of ammonium heptamolybdate [$(NH_4)_6Mo_7O_{24}\cdot 4H_2O$], 30.48 g of ammonium metavanadate ($NH_4VO_3$) and 49.15 g of telluric acid ($H_6TeO_6$), and the resultant mixture was heated to 60° C. while stirring, to thereby obtain an aqueous mixture ($a_5$).

On the other hand, to 170 g of water were added 19.38 g of niobic acid ($Nb_2O_5$ content: 76.6% by weight), 22.53 g of oxalic acid dehydrate ($H_2C_2O_4\cdot 2H_2O$) and 16.43 g of citric acid monohydrate ($H_8C_6O_7\cdot H_2O$), and the resultant mixture was heated to 80° C. while stirring, followed by cooling to 30° C. The resultant cooled mixture was stirred for 8 hours to dissolve the niobic acid, oxalic acid dehydrate and citric acid monohydrate in the water, to thereby obtain an aqueous niobium-oxalic acid-citric acid solution.

To the above-prepared aqueous mixture ($a_5$) was added 202 g of a silica sol having an $SiO_2$ content of 30% by weight, and the resultant mixture was cooled to 30° C. To the resultant cooled mixture was added the above-prepared aqueous niobium-oxalic acid-citric acid solution, to thereby obtain an aqueous raw material mixture. The complex formation ratio (R) was determined in substantially the same manner as in Example 1, except that the value of S2 was determined with respect to an aqueous raw material mixture prepared by the same procedure as described above in this Example wherein, however, 1.5 g of water was used instead of citric acid monohydrate (i.e., the complexing agent used in the method of the present invention). It was found that S1=112 mmole, S2=2.2 mmole and S3=112 mmole, so that R was found to be 100 mole %.

The obtained aqueous raw material mixture was subjected to a spray drying by means of a centrifugation type spray-drying apparatus under conditions wherein the entrance and exit temperatures of the dryer of the spray-drying apparatus were 240° C. and 145° C., respectively, to thereby obtain a dried powder comprised of spherical particles. The obtained dried powder was subjected to a pre-calcination at 330° C. for 2 hours in an atmosphere of air, to thereby obtain a catalyst precursor. The obtained catalyst precursor was calcined under substantially the same conditions as employed in Example 1 for calcination of the dry powder, except that the calcination temperature was 600° C., to thereby to thereby obtain an oxide catalyst. The composition of the oxide catalyst and the important conditions of the catalyst production process are shown in Table 1.

Ammoxidation of Propane 0.35 g of the obtained oxide catalyst (W=0.35 g) was charged into a fixed-bed type reaction tube having an inner diameter of 4 mm. A gaseous feedstock mixture having a molar ratio of propane:ammonia:oxygen:helium of 1:1.2:2.8:15.5 was fed into the reaction tube at a flow rate (F) of 7.0 (ml/min). The reaction temperature (T) was 420° C. and the reaction pressure (P) was 0 MPa in terms of the gauge pressure. The contact time between the oxide catalyst and the gaseous mixture of the feedstocks was 1.2 (g·sec/ml). The produced gaseous reaction mixture was analyzed by means of an on-line gas chromatography apparatus. The results are shown in Table 1.

COMPARATIVE EXAMPLE 6

Preparation of a Catalyst

An oxide catalyst was prepared in substantially the same manner as in Example 7, except that the addition of citric acid monohydrate was omitted. The complex formation ratio (R) was determined in the same manner as in Example 7. It was found that S1=2.2 mmole, S2=2.2 mmole and S3=112 mmole, so that R was found to be 0 mole % (in this Comparative Example, S2=S1). The composition of the oxide catalyst and the important conditions of the catalyst production process are shown in Table 1.

Ammoxidation of Propane

Using the obtained oxide catalyst, the ammoxidation of propane was performed in substantially the same manner as in Example 7, except that the flow rate (F) of the gaseous feedstock mixture was changed to 4.5 (ml/min) and the contact time was changed to 1.8 (g·sec/ml). The results of the ammoxidation are shown in Table 1.

COMPARATIVE EXAMPLE 7

Preparation of a Catalyst

Preparation of an oxide catalyst was performed in substantially the same manner as in Comparative Example 6, except that the amount of oxalic acid dihydrate used to obtain an aqueous niobium-oxalic acid-citric acid solution was changed from 22.53 g to 37.55 g. The complex formation ratio (R) was determined in the same manner as in Example 7. It was found that S1=2.2 mmole, S2=2.2 mmole and S3=112 mmole, so that R was found to be 0 mole % (in this Comparative Example, S2=S1). The composition of the oxide catalyst and the important conditions of the catalyst production process are shown in Table 1.

Table 1 shows that, in Example 7, the amount of the water-soluble Nb atoms (i.e., S1) was remarkably large, as compared to those in Comparative Examples 6 and 7.

Ammoxidation of Propane

Using the obtained oxide catalyst, the ammoxidation of propane was performed in substantially the same manner as in Example 7, except that the flow rate (F) of the gaseous feedstock mixture was changed to 4.5 (ml/min) and the contact time was changed to 1.8 (g·sec/ml). The results are shown in Table 1.

EXAMPLE 8

Preparation of a Catalyst

An oxide catalyst represented by the formula: $Mo_1V_{0.31}Sb_{0.22}Nb_{0.05}O_n$ was prepared as follows.

Substantially the same procedure for preparing an oxide catalyst as in Example 1 was repeated, except that the amount of antimony (III) oxide used to prepare an aqueous mixture ($a_1$) was changed from 41.3 g to 45.4 g, that the amount of 5 wt % aqueous hydrogen peroxide was changed from 193 g to 212 g, and that the addition of the silica sol was omitted, to thereby obtain an oxide catalyst having a composition represented by the above formula. The complex formation ratio (R) was determined in the same manner as in Example 1. It was found that S1=70.9 mmole, S2=3.0 mmole and S3=70.9 mmole, so that R was found to be 100 mole %. The composition of the oxide catalyst and the important conditions of the catalyst production process are shown in Table 2.

Oxidation of Propane 0.35 g of the obtained oxide catalyst (W=0.35 g) was charged into a fixed-bed type reaction tube having an inner diameter of 4 mm. A gaseous feedstock mixture having a molar ratio of propane:oxygen:steam:helium of 1:3.1:14.0:10.0 was fed into the reaction tube at a flow rate (F) of 7.0 (ml/min). The reaction temperature (T) was 380° C. and the reaction pressure (P) was 0 MPa in terms of the gauge pressure. The contact time between the oxide catalyst and the gaseous mixture of the feedstocks was 1.2 (g·sec/ml). The results are shown in Table 2.

COMPARATIVE EXAMPLE 8

Preparation of a Catalyst

Preparation of an oxide catalyst was performed in substantially the same manner as in Example 8, except that the addition of the aqueous hydrogen peroxide was omitted. The complex formation ratio (R) was determined in the same manner as in Example 1. It was found that S1=2.8 mmole, S2=2.8 mmole and S3=70.9 mmole, so that R was found to be 0 mole % (in this Comparative Example, S2=S1). The composition of the oxide catalyst and the important conditions of the catalyst production process are shown in Table 2.

Table 2 shows that, in Example 8, the amount of the water-soluble Nb atoms (i.e., S1) was remarkably large, as compared to that in Comparative Example 8.

Oxidation of Propane

Using the obtained oxide catalyst, the oxidation of propane was performed in substantially the same manner as in Example 8, except that the flow rate (F) of the gaseous feedstock mixture was changed to 4.5 (ml/min) and the contact time was changed to 2.0 (g·sec/ml). The results are shown in Table 2.

EXAMPLE 9

Oxidation of Propane

Using the oxide catalyst obtained in Example 5, the oxidation of propane was performed in substantially the same manner as in Example 8, except that the flow rate (F) of the gaseous feedstock mixture was changed to 8 (ml/min) and the contact time was changed to 1.1 (g·sec/ml). The results are shown in Table 2.

COMPARATIVE EXAMPLE 9

Oxidation of Propane

Using the oxide catalyst obtained in Comparative Example 4, the oxidation of propane was performed in substantially the same manner as in Example 8, except that the flow rate (F) of the gaseous feedstock mixture was changed to 5 (ml/min) and the contact time was changed to 1.7 (g·sec/ml). The results are shown in Table 2.

TABLE 1

| | | | | | Ammoxidation of propane | | | |
|---|---|---|---|---|---|---|---|---|
| | Catalyst composition | Complexing agent | R (mole %) | Reaction conditions (1*) | Contact time (g·sec/ml) | Conversion of propane (%) | Selectivity for acrylonitrile (%) | Space time yield of acrylonitrile $\left(\frac{\mu mol}{(g \cdot sec/ml) \cdot g}\right)$ |
| | (*2) | | | | | | | |
| Ex. 1 | $Mo_1V_{0.31}Sb_{0.2}Nb_{0.05}O_n/SiO_2$(40 wt %) | $H_2O_2$ | 100 | C1 | 1.2 | 48.3 | 65.4 | 0.54 |
| Ex. 2 | $Mo_1V_{0.31}Sb_{0.2}Nb_{0.05}O_n/SiO_2$(40 wt %) | $H_2O_2$ | 47 | C1 | 1.6 | 48.5 | 64.8 | 0.40 |
| Ex. 3 | $Mo_1V_{0.31}Sb_{0.2}Nb_{0.05}O_n/SiO_2$(40 wt %) | $H_2O_2$ | 100 | C1 | 1.1 | 48.1 | 65.3 | 0.57 |
| Comp. Ex. 1 | $Mo_1V_{0.31}Sb_{0.2}Nb_{0.05}O_n/SiO_2$(40 wt %) | — | 0 | C1 | 2.1 | 48.5 | 63.9 | 0.30 |
| Comp. Ex. 2 | $Mo_1V_{0.31}Sb_{0.2}Nb_{0.05}O_n/SiO_2$(40 wt %) | — | 0 | C1 | 2.1 | 48.6 | 63.8 | 0.30 |
| Ex. 4 | $Mo_1V_{0.31}Sb_{0.17}Nb_{0.05}O_n/SiO_2$(40 wt %) | $H_2O_2$ | 100 | C1 | 1.2 | 48.5 | 65.2 | 0.54 |
| Comp. Ex. 3 | $Mo_1V_{0.31}Sb_{0.17}Nb_{0.05}O_n/SiO_2$(40 wt %) | — | 0 | C1 | 2.1 | 48.6 | 63.2 | 0.30 |
| Ex. 5 | $Mo_1V_{0.33}Te_{0.22}Nb_{0.11}O_n$ | $H_2O_2$ | 100 | C2 | 0.8 | 90.7 | 62.9 | 0.66 |
| Comp. Ex. 4 | $Mo_1V_{0.33}Te_{0.22}Nb_{0.11}O_n$ | — | 0 | C2 | 1.2 | 90.8 | 61.8 | 0.43 |
| Ex. 6 | $Mo_1V_{0.33}Te_{0.22}Nb_{0.12}O_n/SiO_2$(30 wt %) | $H_2O_2$ | 100 | C3 | 2.3 | 85.1 | 61.9 | 0.23 |
| Comp. Ex. 5 | $Mo_1V_{0.33}Te_{0.22}Nb_{0.12}O_n/SiO_2$(30 wt %) | — | 0 | C3 | 3.0 | 85.4 | 60.8 | 0.17 |
| Ex. 7 | $Mo_1V_{0.28}Te_{0.23}Nb_{0.12}O_n/SiO_2$(23 wt %) | citric acid | 100 | C4 | 1.2 | 86.4 | 62.8 | 0.39 |
| Comp. Ex. 6 | $Mo_1V_{0.28}Te_{0.23}Nb_{0.12}O_n/SiO_2$(23 wt %) | — | 0 | C4 | 1.8 | 40.3 | 45.0 | 0.08 |
| Comp. Ex. 7 | $Mo_1V_{0.28}Te_{0.23}Nb_{0.12}O_n/SiO_2$(23 wt %) | — | 0 | C4 | 1.8 | 86.3 | 60.3 | 0.24 |

Notes for Table 1:
(*1) C1 Composition of the gaseous feedstock mixture: [propane:ammonia:oxygen:helium] molar ratio = 1:0.7:1.7:5.3 Reaction temperature: 420° C.; Reactor: Fixed-bed reactor
C2 Composition of the gaseous feedstock mixture: [propane:ammonia:oxygen:helium] molar ratio = 1:1.2:3.0:14.8 Reaction temperature: 420° C.; Reactor: Fixed-bed reactor
C3 Composition of the gaseous feedstock mixture: [propane:ammonia:oxygen:helium] molar ratio = 1:1.2:3.0:12.0 Reaction temperature: 430° C.; Reactor: Fluidized-bed reactor
C4 Composition of the gaseous feedstock mixture: [propane:ammonia:oxygen:helium] molar ratio = 1:1.2:2.8:15.5 Reaction temperature: 420° C.; Reactor: Fixed-bed reactor
(*2) In the column "Catalyst composition", the number in the parentheses is the amount (% by weight) of the silica carrier in terms of $SiO_2$, based on the total weight of the oxide catalyst and the silica carrier in terms of $SiO_2$.

TABLE 2

| | | | | | Oxidation of proprane | | | |
|---|---|---|---|---|---|---|---|---|
| | Catalyst composition | Complexing agent | R (mole %) | Reaction conditions (*1) | Contact time (g·sec/ml) | Conversion of propane (%) | Selectivity for acrylic acid (%) | Space time yield of acrylic acid $\left(\frac{\mu mol}{(g \cdot sec/ml) \cdot g}\right)$ |
| Ex. 8 | $Mo_1V_{0.31}Sb_{0.22}Nb_{0.05}O_n$ | $H_2O_2$ | 100 | C5 | 1.3 | 63.1 | 52.9 | 0.18 |
| Comp. Ex. 8 | $Mo_1V_{0.31}Sb_{0.22}Nb_{0.05}O_n$ | — | 0 | C5 | 2.0 | 62.9 | 47.8 | 0.10 |
| Ex. 9 | $Mo_1V_{0.33}Te_{0.22}Nb_{0.11}O_n$ | $H_2O_2$ | 100 | C5 | 1.1 | 64.3 | 53.9 | 0.21 |
| Comp. Ex. 9 | $Mo_1V_{0.33}Te_{0.22}Nb_{0.11}O_n$ | — | 0 | C5 | 1.8 | 64.2 | 48.5 | 0.12 |

Notes:
(*1) C5 Composition of the gaseous feedstock mixture: [propane:oxygen:steam:helium] molar ratio = 1:3.1:14:10
Reaction temperature: 380° C.; Reactor: Fixed-bed reactor

INDUSTRIAL APPLICABILITY

When the ammoxidation or oxidation of propane or isobutane in the gaseous phase is performed in the presence of the oxide catalyst produced by the process of the present invention, (meth)acrylonitrile or (meth)acrylic acid can be produced at a relatively low reaction temperature with high selectivity and in high yield as well as in high space time yield. Further, by the use of the process of the present invention for producing an oxide catalyst, precipitation of the niobium compound (used as one of the raw materials) during the step for producing the aqueous raw material mixture can be reduced or substantially prevented, so that the aqueous raw material mixture can be obtained in the form of a low viscosity slurry having a low solids content or in the form of an aqueous solution. Therefore, the process of the present invention for producing an oxide catalyst is advantageous not only in that the motive power needed for agitation in tanks for producing or storing the aqueous raw material mixture can be reduced, but also in that precipitation of the niobium compound in the tanks or transfer pipes (which causes disadvantageous phenomena, such as formation of an aqueous raw material mixture having a non-uniform compositional distribution and occurrence of a clogging in the tanks or transfer pipes) can be reduced or substantially prevented without using any special equipment. Therefore, by the process of the present invention, the production of an oxide catalyst can be performed efficiently, as compared to the case of the use of conventional processes for producing an oxide catalyst.

What is claimed is:

1. A process for producing an oxide catalyst for use in a catalytic oxidation or ammoxidation of propane or isobutane in the gaseous phase, wherein said oxide catalyst comprises a composition represented by the following formula (I)

$$Mo_{1.0}V_aX_bNb_cZ_dO_n \qquad (I)$$

wherein:
X is at least one element selected from the group consisting of antimony and tellurium;
Z is at least one element selected from the group consisting of tungsten, chromium, titanium, aluminum, tantalum, zirconium, hafnium, manganese, rhenium, iron, ruthenium, cobalt, rhodium, nickel, palladium, platinum, zinc, boron, gallium, indium, germanium, tin, phosphorus, lead, bismuth, yttrium, rare earth elements and alkaline earth metals; and
a, b, c, d, and n are, respectively, the atomic ratios of vanadium, X, niobium, Z and oxygen, relative to molybdenum,
wherein
$0.01 \leq a \leq 100$;
$0.01 \leq b \leq 100$;
$0.01 \leq c \leq 100$;
$0 \leq d \leq 100$; and
n is a number determined by the valence requirements of the other elements present, said process comprising providing an aqueous raw material mixture containing compounds of the component elements of the composition of said formula (I), and drying said aqueous raw material mixture, followed by calcination, wherein, in said aqueous raw material mixture, at least a part of the niobium compound as one of the compounds of said component elements is present in the form of a complex thereof with a complexing agent comprising a compound having a hydroxyl group bonded to an oxygen atom or a carbon atom.

2. The process according to claim 1, wherein said aqueous raw material mixture has a complex formation ratio (R) of 20 mole % or more, said complex formation ratio (R) being defined by the following formula (II):

$$R(\text{mole \%}) = ((S1-S2)/(S3-S2)) \times 100 \qquad (II)$$

wherein S1 represents the molar amount of the water-soluble niobium atoms in the aqueous raw material mixture, S2 represents the molar amount of the water-soluble niobium atoms which are not ascribed to the formation of the complex, and S3 represents the total molar amount of water-soluble niobium atoms and water-insoluble niobium atoms in the aqueous raw material mixture.

3. The process according to claim 1 or 2, wherein said niobium compound is a niobium dicarboxylate.

4. The process according to claim 3, wherein said niobium dicarboxylate is a compound which is formed by dissolving niobic acid in an aqueous dicarboxylic acid solution.

5. The process according to claim 1, wherein said complexing agent comprises at least one compound selected from the group consisting of hydrogen peroxide and a monooxypolycarboxylic acid.

6. The process according to claim 4, wherein said aqueous raw material mixture is obtained by a process comprising:
dissolving niobic acid in an aqueous dicarboxylic acid solution to obtain an aqueous niobium dicarboxylate solution,
mixing the obtained aqueous niobium dicarboxylate solution with said complexing agent or an aqueous solution of said complexing agent to obtain an aqueous niobium dicarboxylate/complexing agent solution, and
mixing the obtained aqueous niobium dicarboxylate/complexing agent solution with a single aqueous mixture or two or more aqueous mixtures containing compounds of said component elements other than niobium to thereby obtain said aqueous raw material mixture.

7. The process according to claim 4, wherein said aqueous raw material mixture is obtained by a process comprising:
mixing said complexing agent or an aqueous solution of said complexing agent with a single aqueous mixture or two or more aqueous mixtures containing compounds of said component elements other than niobium to obtain a complexing agent-containing aqueous non-niobium element compound mixture, and
mixing the obtained complexing agent-containing aqueous non-niobium element compound mixture with an aqueous niobium dicarboxylate solution obtained by dissolving niobic acid in an aqueous dicarboxylic acid solution, to thereby obtain said aqueous raw material mixture.

8. The process according to claim 1 or 2, wherein said complexing agent is hydrogen peroxide.

9. The process according to claim 3, wherein said niobium dicarboxylate is niobium oxalate.

10. The process according to claim 1 or 2, wherein said aqueous raw material mixture further contains a source of silica in an amount such that said oxide catalyst further comprises a silica carrier having supported thereon said oxide catalyst, wherein said silica carrier is present in an amount of from 20 to 60% by weight, based on the total weight of said oxide catalyst and said silica carrier.

11. A process for producing acrylonitrile or methacrylonitrile, comprising reacting propane or isobutane with ammonia and molecular oxygen in the gaseous phase in the presence of the oxide catalyst produced by the process of claim 1 or 2.

12. A process for producing acrylic acid or methacrylic acid, comprising reacting propane or isobutane with molecular oxygen in the gaseous phase in the presence of the oxide catalyst produced by the process of claim 1 or 2.

13. A process for producing an oxide catalyst for use in a catalytic oxidation or ammoxidation of propane or isobutane in the gaseous phase,
wherein said oxide catalyst comprises a composition represented by the following formula (I):

$$MO_{1.0}V_aX_bNb_cZ_dO_n \quad (I)$$

wherein:
X is at least one element selected from the group consisting of antimony and tellurium;
Z is at least one element selected from the group consisting of tungsten, chromium, titanium, aluminum, tantalum, zirconium, hafnium, manganese, rhenium, iron, ruthenium, cobalt, rhodium, nickel, palladium, platinum, zinc, boron, gallium, indium, germanium, tin, phosphorus, lead, bismuth, yttrium, rare earth elements and alkaline earth metals; and
a, b, c, d, and n are, respectively, the atomic ratios of vanadium, X, niobium, Z and oxygen, relative to molybdenum,
wherein
$0.01 \leq a \leq 100$;
$0.01 \leq b \leq 100$;
$0.0 \leq c \leq 100$;
$0 \leq d \leq 100$; and
n is a number determined by the valence requirements of the other elements present,
said process comprising providing an aqueous raw material mixture containing compounds of the component elements of the composition of said formula (I), and drying said aqueous raw material mixture, followed by calcination, wherein, in said aqueous raw material mixture, at least a part of the niobium compound as one of the compounds of said component elements is present in the form of a complex thereof with a complexing agent comprising a compound having a hydroxyl group bonded to an oxygen atom or a carbon atom, wherein said complexing agent comprises at least one compound selected from the group consisting of hydrogen peroxide and a monooxypolycarboxylic acid, and wherein said aqueous raw material mixture has a complex formation ratio (R) of 20 mole % or more, said complex formation ratio (R) being defined by the following formula (II)

$$R \text{ (mole \%)} = ((S1-S2)/(S3-S2)) \times 100 \quad (II)$$

wherein S1 represents the molar amount of the water-soluble niobium atoms in the aqueous raw material mixture, S2 represents the molar amount of the water-soluble niobium atoms which are not ascribed to the formation of the complex, and S3 represents the total molar amount of water-soluble niobium atoms and water-insoluble niobium atoms in the aqueous raw material mixture.

* * * * *